US009045417B2

(12) United States Patent
Man et al.

(10) Patent No.: US 9,045,417 B2
(45) Date of Patent: Jun. 2, 2015

(54) ISOTOPOLOGUES OF ISOINDOLE DERIVATIVES

(75) Inventors: Hon-Wah Man, Princeton, NJ (US); Louise Michelle Cameron, Nazareth, PA (US); Anthony Joseph Frank, Easton, PA (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 13/979,602

(22) PCT Filed: Jan. 12, 2012

(86) PCT No.: PCT/US2012/021016
§ 371 (c)(1),
(2), (4) Date: Feb. 26, 2014

(87) PCT Pub. No.: WO2012/097116
PCT Pub. Date: Jul. 19, 2012

(65) Prior Publication Data
US 2014/0194485 A1  Jul. 10, 2014

Related U.S. Application Data

(60) Provisional application No. 61/433,123, filed on Jan. 14, 2011.

(51) Int. Cl.
*A61K 31/4035* (2006.01)
*C07D 209/44* (2006.01)
*C07D 209/48* (2006.01)
*A61K 45/06* (2006.01)
*C07D 209/66* (2006.01)
*C07D 209/46* (2006.01)
*C07D 209/49* (2006.01)

(52) U.S. Cl.
CPC .............. *C07D 209/48* (2013.01); *A61K 45/06* (2013.01); *C07D 209/66* (2013.01); *A61K 31/4035* (2013.01); *C07D 209/46* (2013.01); *C07D 209/49* (2013.01)

(58) Field of Classification Search
CPC ............................ C07D 209/44; C07D 209/48
USPC ........................... 548/478, 472; 514/416, 417
See application file for complete search history.

(56) References Cited

U.S. PATENT DOCUMENTS

2010/0324108 A1   12/2010   Liu

FOREIGN PATENT DOCUMENTS

WO    2006/259991 A2    3/2006
WO    2010/147922 A1    12/2010

OTHER PUBLICATIONS

Liu. Document No. 154:64629, retrieved from CAPLUS, Dec. 23, 2010.*
Vippagunta, et al. Advanced Drug Delivery Reviews 48 (2001) 3-26.*
Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*

* cited by examiner

*Primary Examiner* — Shawquia Jackson
(74) *Attorney, Agent, or Firm* — Jones Day

(57) ABSTRACT

Provided herein are isoindole derivatives, which is enriched with isotopes such as deuterium. Pharmaceutical compositions comprising the isotopes-enriched compounds, and methods of using such compounds are also provided.

10 Claims, No Drawings

ISOTOPOLOGUES OF ISOINDOLE DERIVATIVES

The present application is a 371 of International Application No. PCT/US2012/021016, filed Jan. 12, 2012, which claims priority to U.S. Provisional Patent Application No. 61/433,123, filed Jan, 14, 2011, the entirety of each of which is incorporated herein by reference.

1. FIELD

Provided herein are isotopologues of certain isoindole derivatives, compositions comprising the isotopologues, methods of making the isotopologues, and methods of their use for treatment or prevention of diseases and conditions including, but not limited to, inflammatory diseases, autoimmune diseases, and cancers.

2. BACKGROUND

Tumor necrosis factor alpha, (TNF-α) is a cytokine that is released primarily by mononuclear phagocytes in response to immunostimulators. TNF-α is capable of enhancing most cellular processes, such as differentiation, recruitment, proliferation, and proteolytic degradation. At low levels. TNF-α confers protection against infective agents, tumors, and tissue damage. But TNF-α also has a role in many diseases. When administered to mammals or humans, TNF-α causes or aggravates inflammation, fever, cardiovascular effects, hemorrhage, coagulation, and acute phase responses similar to those seen during acute infections and shock states. Enhanced or unregulated TNF-α production has been implicated in a number of diseases and medical conditions, for example, cancers, such as solid tumors and blood-born tumors; heart disease, such as congestive heart failure; and viral, genetic, inflammatory, allergic, and autoimmune diseases.

Adenosine 3',5'-cyclic monophosphate (cAMP) also plays a role in many diseases and conditions, such as but not limited to asthma and inflammation, and other conditions (Lowe and Cheng, Drugs of the Future, 17(9), 799-807, 1992). It has been shown that the elevation of cAMP in inflammatory leukocytes inhibits their activation and the subsequent release of inflammatory mediators, including TNF-α and NF-κB. Increased levels of cAMP also leads to the relaxation of airway smooth muscle.

It is believed that the primary cellular mechanism for the inactivation of cAMP is the breakdown of cAMP by a family of isoenzymes referred to as cyclic nucleotide phosphodiesterases (PDE) (Beavo and Reitsnyder, Trends in Pharm., 11, 150-155, 1990). There are eleven known PDE families. It is recognized, for example, that the inhibition of PDE type IV is particularly effective in both the inhibition of inflammatory mediator release and the relaxation of airway smooth muscle (Verghese, et al., Journal of Pharmacology and Experimental Therapeutics, 272(3), 1313-1320, 1995). Thus, compounds that inhibit PDE4 (PDE IV) specifically, may inhibit inflammation and aid the relaxation of airway smooth muscle with a minimum of unwanted side effects, such as cardiovascular or anti-platelet effects. Currently used PDE4 inhibitors lack the selective action at acceptable therapeutic doses.

Cancer is a particularly devastating disease, and increases in blood TNF-α levels are implicated in the risk of and the spreading of cancer. Normally, in healthy subjects, cancer cells fail to survive in the circulatory system, one of the reasons being that the lining of blood vessels acts as a barrier to tumor-cell extravasation. But increased levels of cytokines have been shown to substantially increase the adhesion of cancer cells to endothelium in vitro. One explanation is that cytokines, such as TNF-α, stimulate the biosynthesis and expression of a cell surface receptors called ELAM-1 (endothelial leukocyte adhesion molecule). ELAM-1 is a member of a family of calcium-dependent cell adhesion receptors, known as LEC-CAMs, which includes LECAM-1 and GMP-140. During an inflammatory response. ELAM-1 on endothelial cells functions as a "homing receptor" for leukocytes. Recently. ELAM-1 on endothelial cells was shown to mediate the increased adhesion of colon cancer cells to endothelium treated with cytokines (Rice et al., 1989, Science 246:1303-1306).

Inflammatory diseases such as arthritis, related arthritic conditions (e.g., osteoarthritis and rheumatoid arthritis), inflammatory bowel disease (e.g. Crohn's disease and ulcerative colitis), sepsis, psoriasis, atopic dermatitis, contact dermatitis, and chronic obstructive pulmonary disease, chronic inflammatory pulmonary diseases are also prevalent and problematic ailments. TNF-α plays a central role in the inflammatory response and the administration of their antagonists block chronic and acute responses in animal models of inflammatory disease.

Enhanced or unregulated TNF-α production has been implicated in viral, genetic, inflammatory, allergic, and autoimmune diseases. Examples of such diseases include but are not limited to: HIV; hepatitis; adult respiratory distress syndrome; bone-resorption diseases; chronic obstructive pulmonary diseases; chronic pulmonary inflammatory diseases; asthma, dermatitis; cystic fibrosis; septic shock; sepsis; endotoxic shock; hemodynamic shock; sepsis syndrome; post ischemic reperfusion injury; meningitis; psoriasis; fibrotic disease; cachexia; graft rejection; auto-immune disease; rheumatoid spondylitis; arthritic conditions, such as rheumatoid arthritis and osteoarthritis; osteoporosis; Crohn's disease; ulcerative colitis; inflammatory-bowel disease; multiple sclerosis; systemic lupus erythrematosus; ENL in leprosy; radiation damage; asthma; and hyperoxic alveolar injury. Tracey et al., 1987, Nature 330:662-664 and Hinshaw et al., 1990, Circ. Shock 30:279-292 (endotoxic shock); Dezube et al., 1990, Lancet. 335:662 (cachexia); Millar et al., 1989, Lancet 2:712-714 and Ferrai-Baliviera et al., 1989, Arch. Surg. 124:1400-1405 (adult respiratory distress syndrome); Bertolini et al., 1986, Nature 319:516-518, Johnson et al., 1989, Endocrinology 124:1424-1427, Holler et al., 1990, Blood 75:1011-1016, and Grau et al., 1989, N. Engl. J. Med. 320:1586-1591 (bone resorption diseases); Pignet et al., 1990, Nature, 344:245-247, Bissonnette et al., 1989, Inflammation 13:329-339 and Baughman et al., 1990, J. Lab. Clin. Med. 115:36-42 (chronic pulmonary inflammatory diseases); Elliot et al., 1995, Int. J. Pharmac. 17:141-145 (rheumatoid arthritis); von Dullemen et al., 1995, Gastroenterology, 109:129-135 (Crohn's disease); Duh et al., 1989, Proc. Nat. Acad. Sci. 86:5974-5978, Poll et al., 1990, Proc. Nat. Acad. Sci. 87:782-785, Monto et al., 1990, Blood 79:2670, Clouse et al., 1989, J. Immunol. 142, 431-438, Poll et al., 1992, AIDS Res. Hum. Retrovirus, 191-197, Poli et al. 1990, Proc. Natl. Acad. Sci. 87:782-784, Folks et al., 1989, PNAS 86:2365-2368 (HIV and opportunistic infections resulting from HIV).

Thus, compounds and compositions that can block the activity or inhibit the production of PDE4 or certain cytokines, including TNF-α, may be beneficial as therapeutics. Many small-molecule inhibitors have demonstrated an ability to treat or prevent inflammatory diseases implicated by PDE4 or TNF-α (for a review, Lowe, 1998 Exp. Opin. Ther. Patents 8:1309-1332).

3. SUMMARY

Embodiments provided herein encompass particular isotopologues of isoindole derivatives provided herein. Certain embodiments encompass mixtures of isotopologues. Certain embodiments encompass methods of synthesizing, isolating, or characterizing the isotopologues.

In certain embodiments, provided herein are pharmaceutical compositions and single unit dosage forms comprising one or more isotopologues of isoindoline derivatives provided herein. Certain embodiments provide methods for the treatment or prevention of particular diseases or disorders, which comprise administering to a patient a therapeutically or prophylactically effective amount of an isotopologue described herein.

4. DETAILED DESCRIPTION

4.1 Definitions

The descriptions of the terminology provided below apply to the terms as used herein and unless otherwise specified.

The term "compound" includes salts and solvates (e.g. hydrates) thereof.

The term "isotopic composition" refers to the amount of each isotope present for a given atom, and "natural isotopic composition" refers to the naturally occurring isotopic composition or abundance for a given atom. Atoms containing their natural isotopic composition may also be referred to herein as "non-enriched" atoms.

Unless otherwise designated, the atoms of the compounds recited herein are meant to represent any stable isotope of that atom. For example, unless otherwise stated, when a position is designated specifically as "H" or "hydrogen," the position is understood to have hydrogen at its natural isotopic composition.

The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. As used herein, an "isotopologue" is an isotopically enriched compound.

The term "isotopic enrichment" refers to the percentage of incorporation of an amount of a specific isotope at a given atom in a molecule in the place of that atom's natural isotopic composition. For example, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%.

The term "isotopic enrichment factor" refers to the ratio between the isotopic composition and the natural isotopic composition of a specified isotope.

With regard to the compounds provided herein, when a particular atomic position is designated as having deuterium or "D," it is understood that the abundance of deuterium at that position is substantially greater than the natural abundance of deuterium, which is about 0.015%. A position designated as having deuterium typically has a minimum isotopic enrichment factor of, in particular embodiments, at least 1000 (15% deuterium incorporation), at least 2000 (30% deuterium incorporation), at least 3000 (45% deuterium incorporation), at least 3500 (52.5% deuterium incorporation), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation) at each designated deuterium atom.

The isotopic enrichment and isotopic enrichment factor of the compounds provided herein can be determined using conventional analytical methods known to one of ordinary skill in the art, including mass spectrometry and nuclear magnetic resonance spectroscopy.

The terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the term refers to the administration of a compound provided herein to a patient subsequent to the onset of a disease provided herein.

The terms "prevent," "preventing" and "prevention" refer to the prevention of the onset, recurrence or spread of a disease or disorder, or of one or more symptoms thereof. In some embodiments, the term refers to the administration of a compound provided herein to a subject who is at a risk of one or more of the diseases provided herein prior to the onset of the diseases. In this regard, the term "prevention" may be equivalent to the term "prophylaxis" or "prophylactic treatment."

The terms "manage," "managing" and "management" refer to preventing or slowing the progression, spread or worsening of a disease or disorder, or of one or more symptoms thereof. In certain cases, the beneficial effects that a subject derives from a prophylactic or therapeutic agent do not result in a cure of the disease or disorder.

A "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

A "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

4.2 Compounds

Provided herein are isotopically enriched compounds, including isotopically enriched isoindole derivatives, synthetic intermediates thereof, and metabolites thereof.

Isotopic enrichment (e.g., deuteration) of pharmaceuticals to improve pharmacokinetics ("PK"), pharmacodynamics ("PD"), and toxicity profiles, has been demonstrated previously with some classes of drugs. (See, e.g., Lijinsky et. al., Food Cosmet. Toxicol., 20: 393 (1982); Lijinsky et. al., J. Nat. Cancer Inst., 69: 1127 (1982); Mangold et. al., Mutation Res.

308: 33 (1994); Gordon et. al., Drug Metab. Dispos., 15: 589 (1987); Zello et. al., Metabolism, 43: 487 (1994); Gately et. al., J. Nucl. Med., 27: 388 (1986); Wade D, Chem. Biol. Interact. 117: 191 (1999)).

Without being limited by a particular theory, isotopic enrichment of a drug can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrease the production of deleterious metabolites in specific tissues and/or create a more effective drug and/or a safer drug for combination therapy, whether the combination therapy is intentional or not.

Replacement of an atom for one of its isotopes may often result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). (See, e.g, Foster et al., Adv. Drug Res., vol. 14, pp. 1-36 (1985); Kushner et al., Can. J. Physiol. Pharmacol., vol. 77, pp. 79-88 (1999)).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. Without being limited by a particular theory, high DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects. Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, may lead to a similar kinetic isotope effect.

The animal body expresses a variety of enzymes for the purpose of eliminating foreign substances, such as therapeutic agents, from its circulation system. Examples of such enzymes include the cytochrome P450 enzymes ("CYPs"), esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) pi-bond. The resultant metabolites may be stable or unstable under physiological conditions, and can have substantially different pharmacokinetic, pharmacodynamic, and acute and long-term toxicity profiles relative to the parent compounds. For many drugs, such oxidations are rapid. These drugs therefore often require the administration of multiple or high daily doses.

Therefore, isotopic enrichment at certain positions of a compound provided herein may produce a detectable KIE that affects the pharmacokinetic, pharmacologic, and/or toxicological profiles of a compound provided herein in comparison with a similar compound having a natural isotopic composition. In one embodiment, the deuterium enrichment is performed on the site of C—H bond cleavage during metabolism.

Certain embodiments herein provide compounds of the following chemical structure:

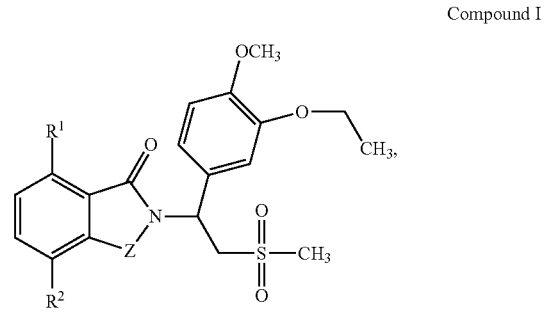

Compound I or a stereoisomer thereof,
wherein at least one of $R^1$ and $R^2$ is hydrogen and the other is $N(H)COR^3$, wherein $R^3$ is $C_1$-$C_3$ alkyl or cyclopropyl;
Z is methylene or C=O; and
wherein one or more hydrogen(s) is/are hydrogen(s) isotopically enriched with deuterium; one or more carbon(s) is/are isotopically enriched with carbon-13; and/or one or both of the nitrogen atom(s) is/are isotopically enriched with nitrogen-15.

4.2.1 2-([1-(3-Ethoxy-4-Methoxyphenyl)-2-Methylsulfonyl Ethyl]-4-Acetylaminoisoindoline-1,3-Dione In one embodiment, provided herein are isotopologues of the following compound:

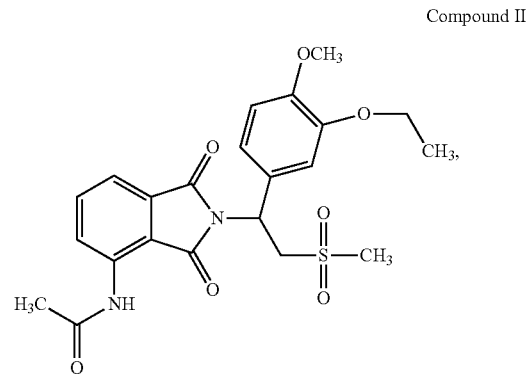 [SMILES: CCOc1cc(C(CS(C)(=O)=O)N2C(=O)c3cccc(NC(C)=O)c3C2=O)ccc1OC]

Compound II or a stereoisomer thereof.

In certain embodiments, one or more hydrogen atoms on the methylsulfonylethyl portion of Compound II are deuterium-enriched. For example, particular compounds provided herein include the following listed compounds, in which the label "D" indicates a deuterium-enriched atomic position. i.e. a sample comprising the given compound has a deuterium enrichment at the indicated position(s) above the natural abundance of deuterium:

Compound II-1
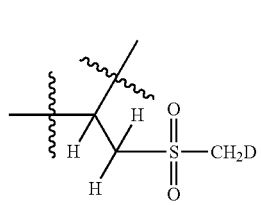

Compound II-2
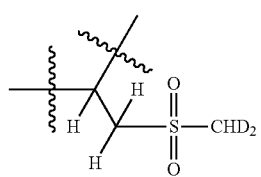

Compound II-3
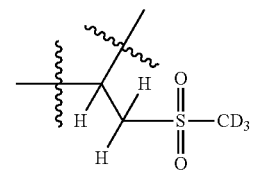

Compound II-4
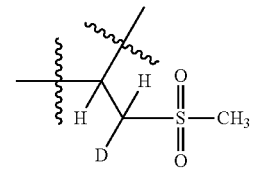

Compound II-5
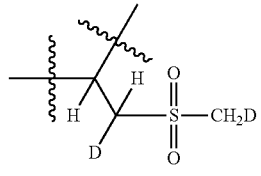

Compound II-6
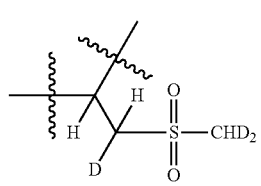

Compound II-7
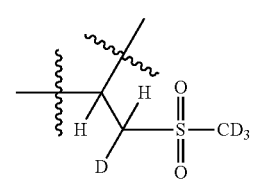

Compound II-8
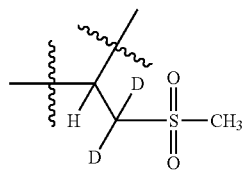

Compound II-9
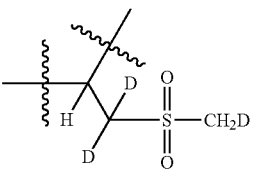

Compound II-10
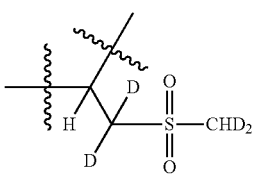

Compound II-11
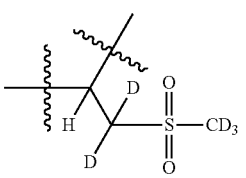

Coumpound II-12
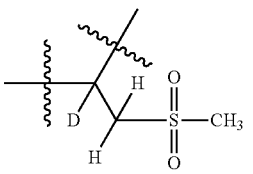

Compound II-13
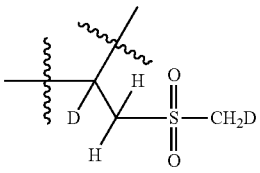

Compound II-14
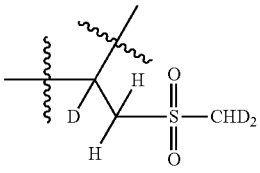

Compound II-15
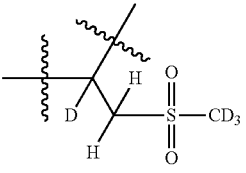

Compound II-16
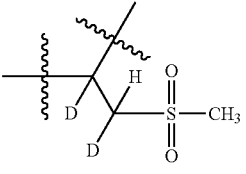

Compound II-17
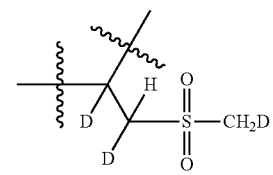

Compound II-18
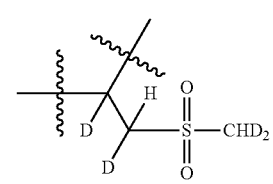

Compound II-19
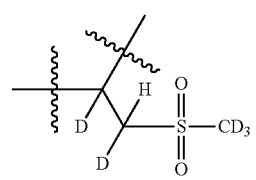

Compound II-20
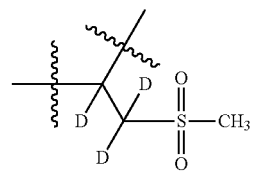

Compound II-21
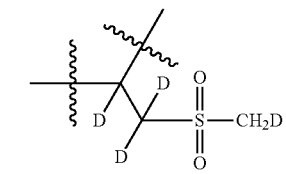

Compound II-22
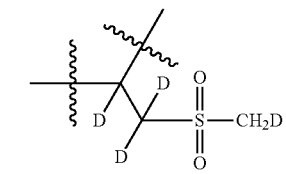 or

Compound II-23
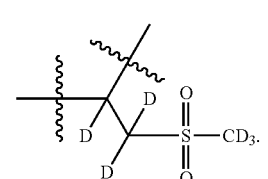

In certain embodiments, one or more hydrogen atoms on the substituents on the phenyl portion of Compound II are deuterium-enriched. For example, particular compounds provided herein include the following listed compounds, in which the label "D" indicates a deuterium-enriched atomic position. i.e. a sample comprising the given compound has a deuterium enrichment at the indicated position(s) above the natural abundance of deuterium:

Compound II-24
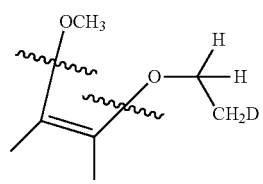

Compound II-25
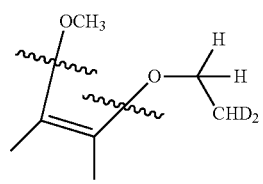

Compound II-26
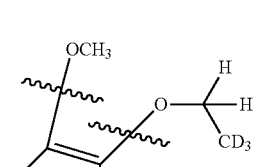

Compound II-27
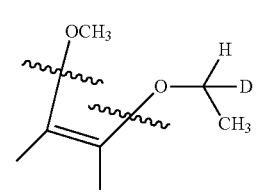

Compound II-28
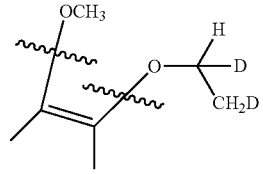

Compound II-29
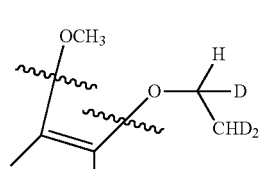

Compound II-30
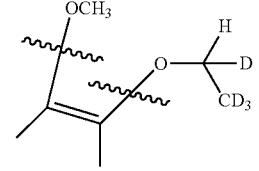

Compound II-31
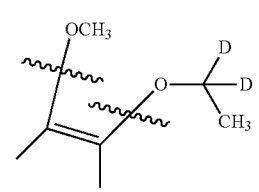

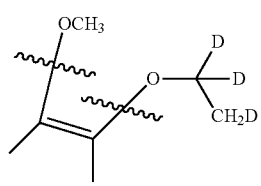
Compound II-32
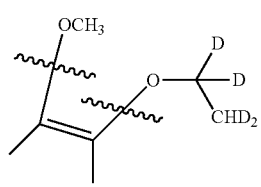
Compound II-33
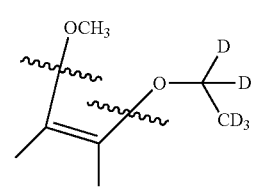
Compound II-34
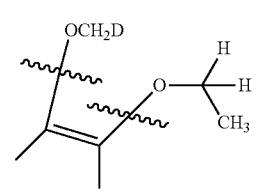
Compound II-35
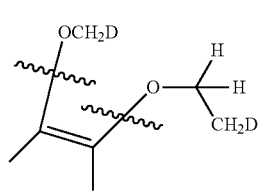
Compound II-36
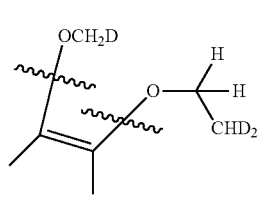
Compound II-37
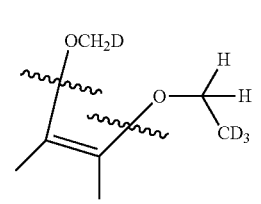
Compound II-38
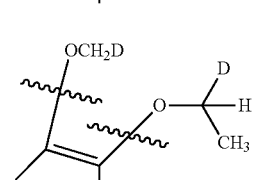
Compound II-39
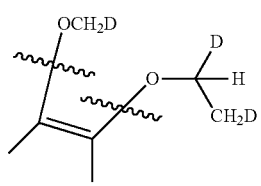
Compound II-40
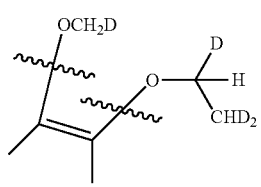
Compound II-41
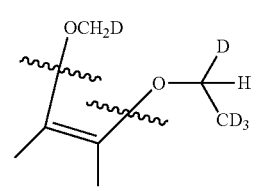
Compound II-42
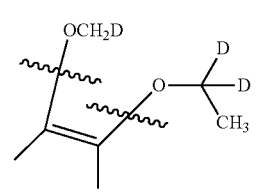
Compound II-43
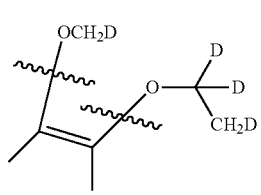
Compound II-44
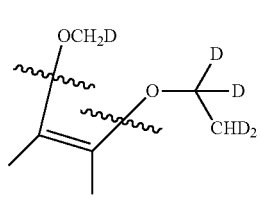
Compound II-45
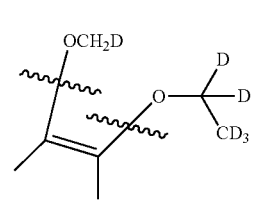
Compound II-46
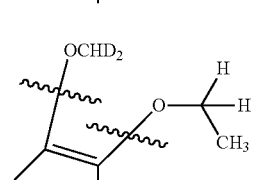
Compound II-47

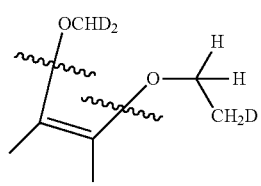
Compound II-48
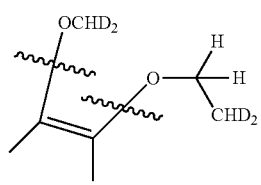
Compound II-49
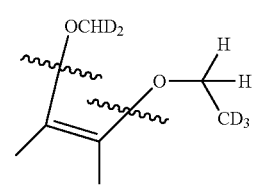
Compound II-50
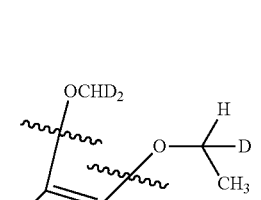
Compound II-51
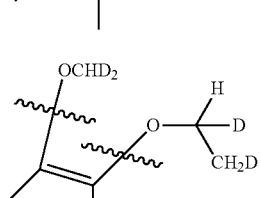
Compound II-52
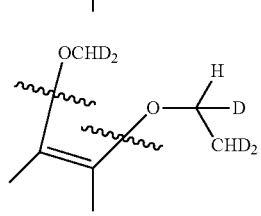
Compound II-53
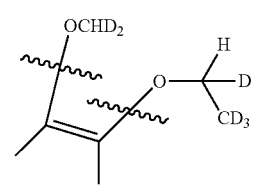
Compound II-54
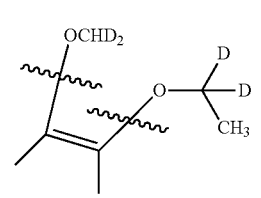
Compound II-55
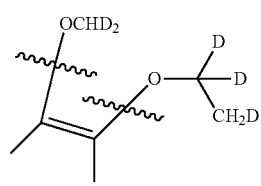
Compound II-56
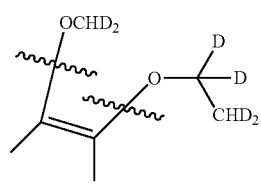
Compound II-57
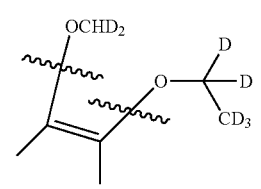
Compound II-58
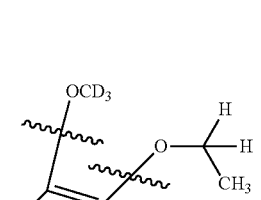
Compound II-59
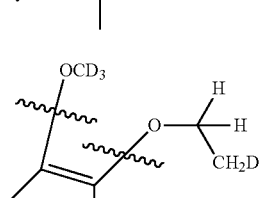
Compound II-60
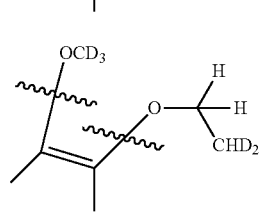
Compound II-61
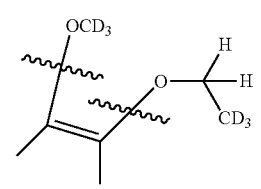
Compound II-62
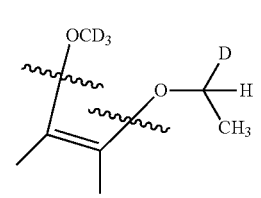
Compound II-63

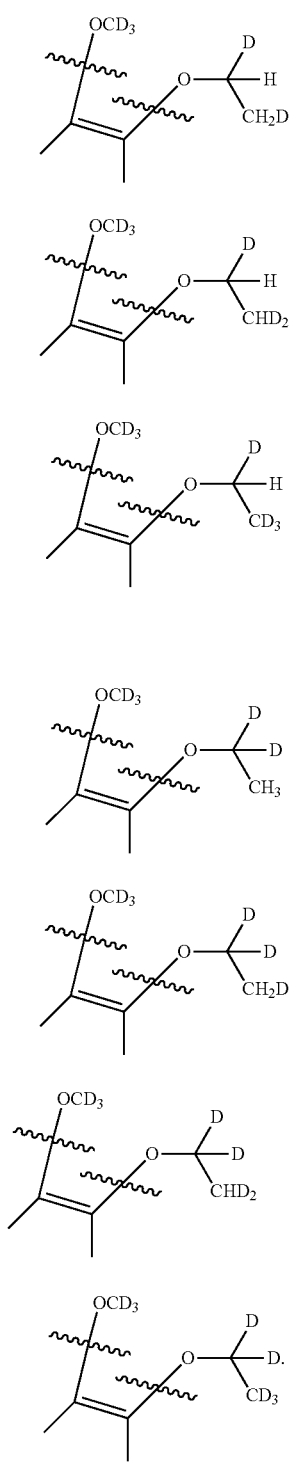

Compound II-64

Compound II-65

Compound II-66

Compound II-67

Compound II-68

Compound II-69 or

Compound II-70

Compound II-71

Compound II-72

Compound II-73

Compound II-74

Compound II-75

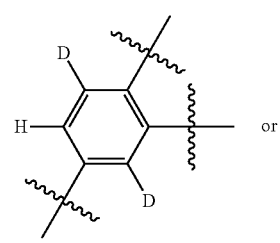

Compound II-76 or

In certain embodiments, one or more hydrogen atoms on the phenyl portion of Compound II are deuterium-enriched. For example, particular compounds provided herein include, but are not limited to the following listed compounds, in which the label "D" indicates a deuterium-enriched atomic position, i.e., a sample comprising the given compound has a deuterium enrichment at the indicated position(s) above the natural abundance of deuterium:

Compound II-77

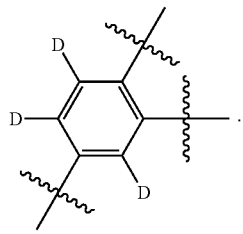

In certain embodiments, one or more hydrogen atoms on the oxoisoindoline portion of Compound II are deuterium-enriched. For example, particular compounds provided herein include, but are not limited to the following listed compounds, in which the label "D" indicates a deuterium-enriched atomic position. i.e. a sample comprising the given compound has a deuterium enrichment at the indicated position(s) above the natural abundance of deuterium:

Compound II-78

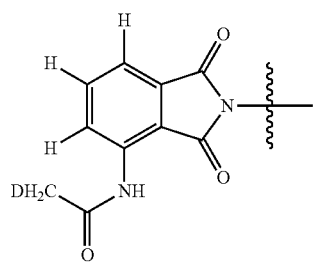

Compound II-79

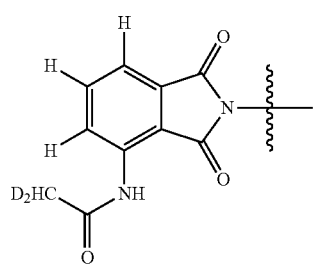

Compound II-80

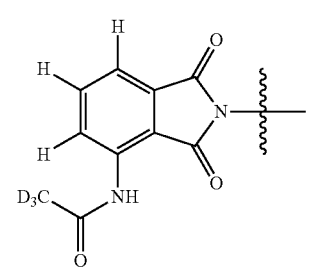

Compound II-81

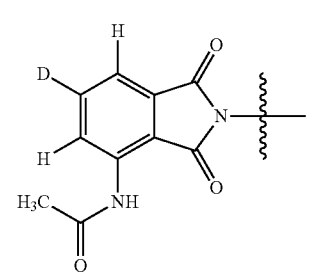

Compound II-82

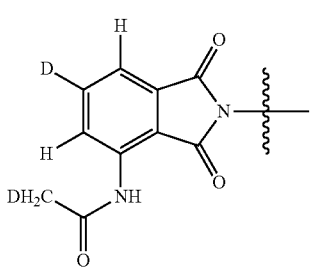

Compound II-83

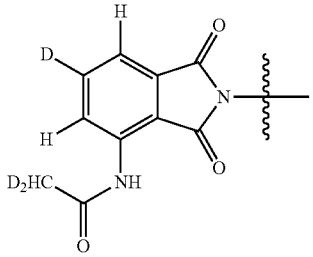

Compound II-84

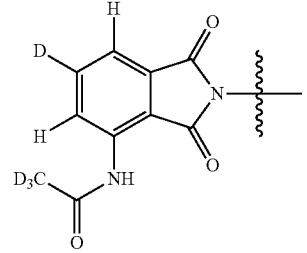

Compound II-85

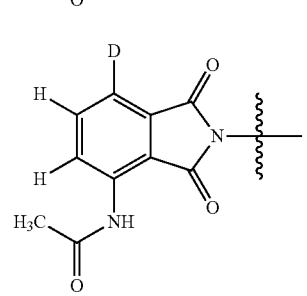

Compound II-86

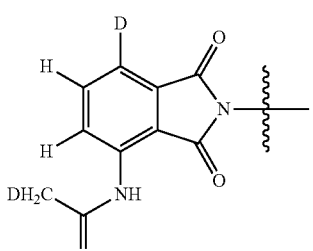

Compound II-87

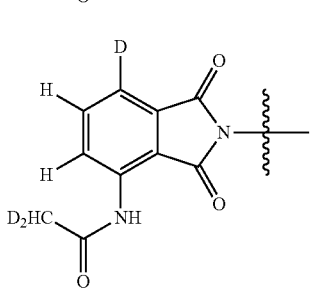

-continued
Compound II-88
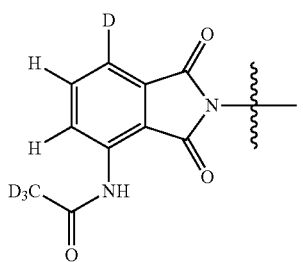
Compound II-89
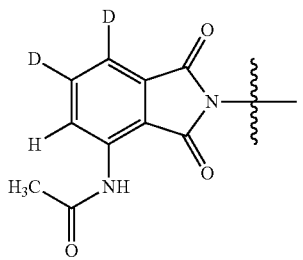
Compound II-90
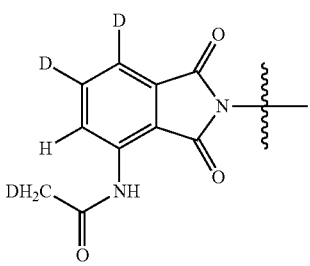
Compound II-91
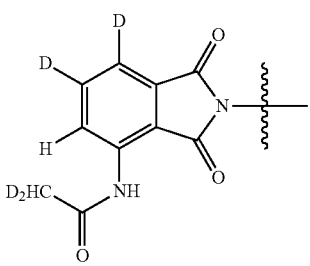
Compound II-92
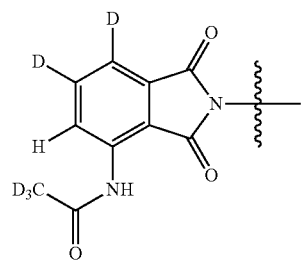
Compound II-93
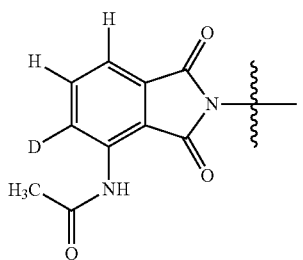
-continued
Compound II-94
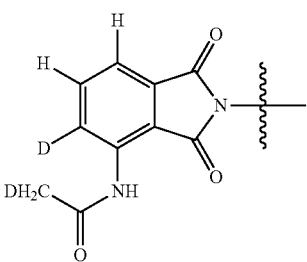
Compound II-95
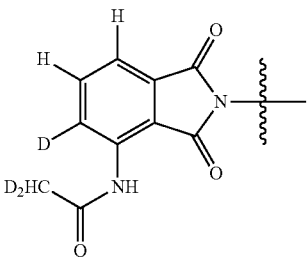
Compound II-96
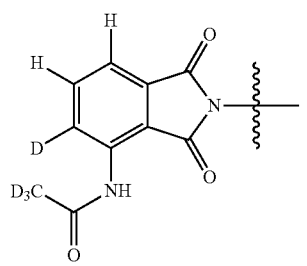
Compound II-97
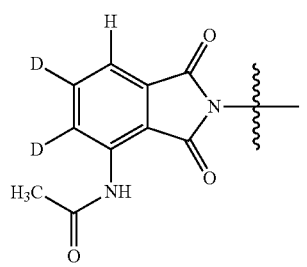
Compound II-98
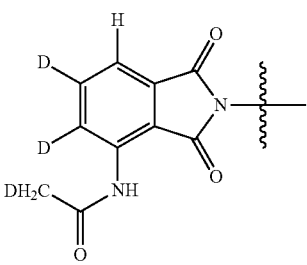
Compound II-99
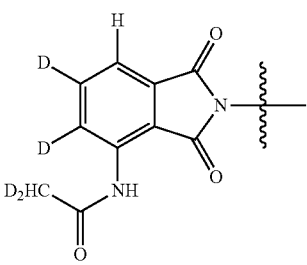

Compound II-100
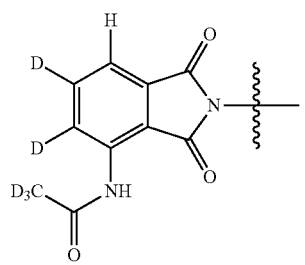

Compound II-101
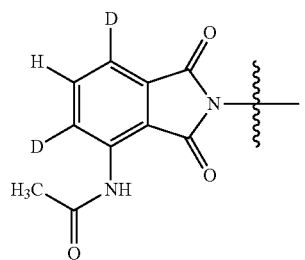

Compound II-101
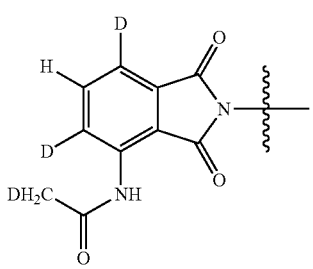

Compound II-102
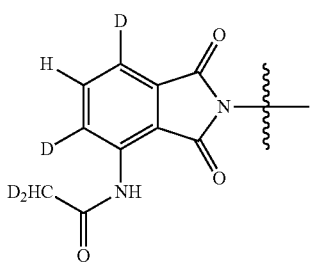

Compound II-103
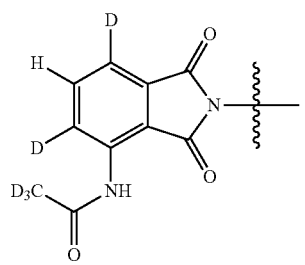

Compound II-104
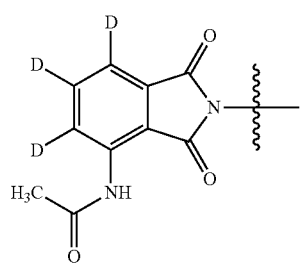

Compound II-105
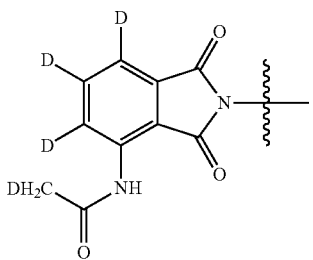

Compound II-106
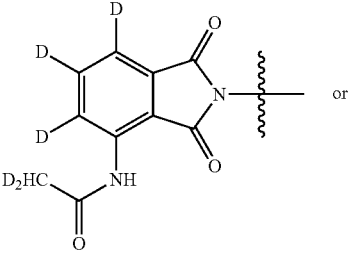

or

Compound II-107
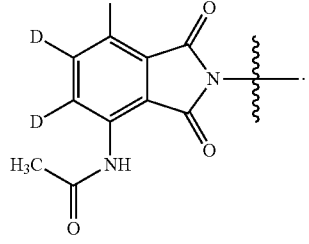

In certain embodiments, one or more hydrogen atoms on any of the portions shown above for Compound II are deuterium-enriched. i.e., any combination of deuteration shown above for Compound II, is encompassed.

It is understood that one or more deuteriums may exchange with hydrogen under physiological conditions.

In some embodiments, provided herein are carbon-13 isotopologues. In certain embodiments, provided herein are compounds of the following chemical structure:

Compound III
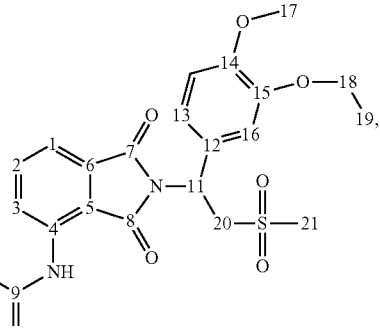

or a stereoisomer thereof,
in which one or more of 1, 2, 3, 4, 5, 6, 7, 8, 9, 10, 1, 12, 13, 14, 15, 16, 17, 19, 19, 20 and 21 is/are carbon atom(s) isotopically enriched with carbon-13, and any remaining carbon atom(s) is/are non-enriched carbon atom(s). In particular embodiments, one, two, three, four, five, six, seven, eight, nine, ten, eleven, twelve, thirteen, fourteen, fifteen, sixteen, seventeen, eighteen, nineteen, twenty or twenty-one of carbon atom(s) 1-21 is are/isotopically enriched with carbon-13, and any remaining carbon atom(s) is/are non-enriched.

In some embodiments, provided herein are nitrogen-15 analogues of Compound II, in which one or more atomic positions of the molecule is isotopically enriched with nitrogen 15. In certain embodiments, provided herein are compounds of the following chemical structure:

Compound IV

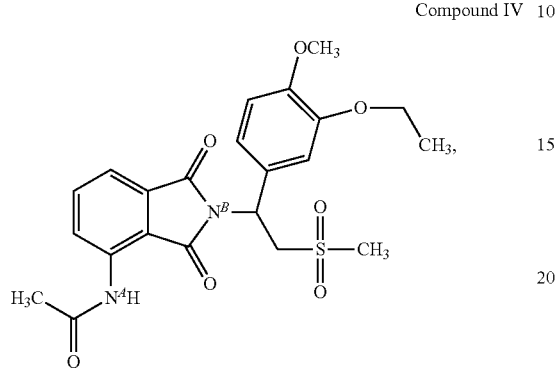

or a stereoisomer thereof, in which one or more of nitrogen atom(s) $N^A$ or $N^B$ is/are isotopically enriched with nitrogen-15, and any remaining nitrogen atom(s) is/are non-enriched nitrogen atom(s). In particular embodiments, one or both of $N^A$ and $N^B$ is/are isotopically enriched with nitrogen-15, and any remaining nitrogen atom(s) is/are non-enriched.

In certain embodiments. $N^A$ is enriched with nitrogen-15. In certain embodiments. $N^B$ is enriched with nitrogen-5. In certain embodiments, $N^A$ and $N^B$ are both enriched with nitrogen-15.

In certain embodiments, one or more hydrogen(s) is/are enriched with deuterium(s) and one or more carbon(s) is/are enriched with carbon-13. In certain embodiments, one or more hydrogen(s) is/are enriched with deuterium and one or more nitrogen(s) is/are enriched with nitrogen-15. In certain embodiments, one or more carbon atom(s) is/are enriched with carbon-13 and one or more nitrogen(s) is/are enriched with nitrogen-15. In certain embodiments, one or more hydrogen(s) is/are enriched with deuterium, one or more carbon(s) are enriched with carbon-13, and one or more nitrogen(s) is/are replaced with nitrogen-15.

In one embodiment, provided herein are isotopologues of the following (S)-isomer of Compound II:

Compound V

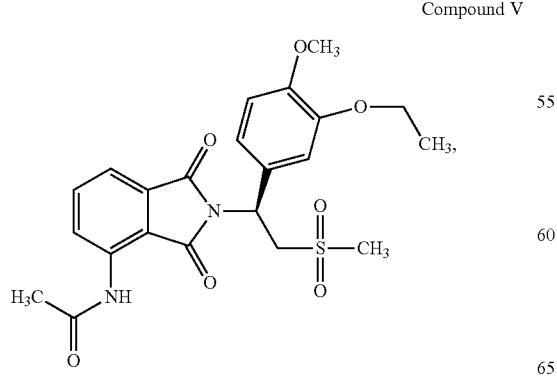

4.2.2 Cyclopropyl N-{2-[(1S)-1-(3-Ethoxy-4-Methoxyphenyl)-2-(Methylsulfonyl)Ethyl]-3-Oxoisoindolin-4-Yl}Carboxamide In one embodiment, provided herein are isotopologues of the following compound:

Compound VI

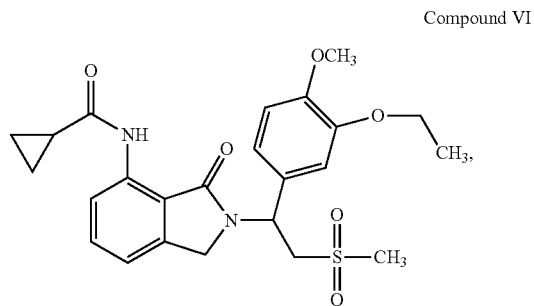 [SMILES: CCOc1cc(C(CS(C)(=O)=O)N2Cc3cccc(NC(=O)C4CC4)c3C2=O)ccc1OC]

or a stereoisomer thereof.

In certain embodiments, one or more hydrogen atoms on the methylsulfonylethyl portion of Compound VI are deuterium-enriched. For example, particular compounds provided herein include the following listed compounds, in which the label "D" indicates a deuterium-enriched atomic position, i.e. a sample comprising the given compound has a deuterium enrichment at the indicated position(s) above the natural abundance of deuterium:

Compound VI-1

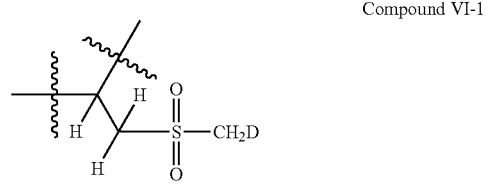

Compound VI-2

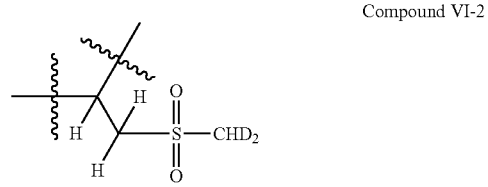

Compound VI-3

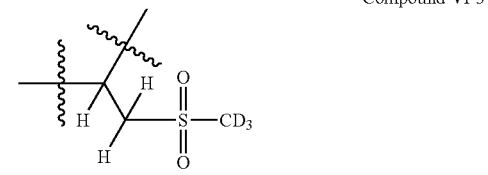

Compound VI-4

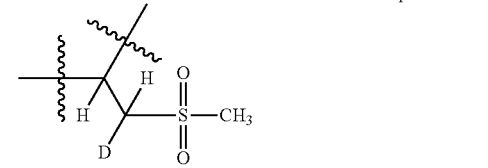

-continued
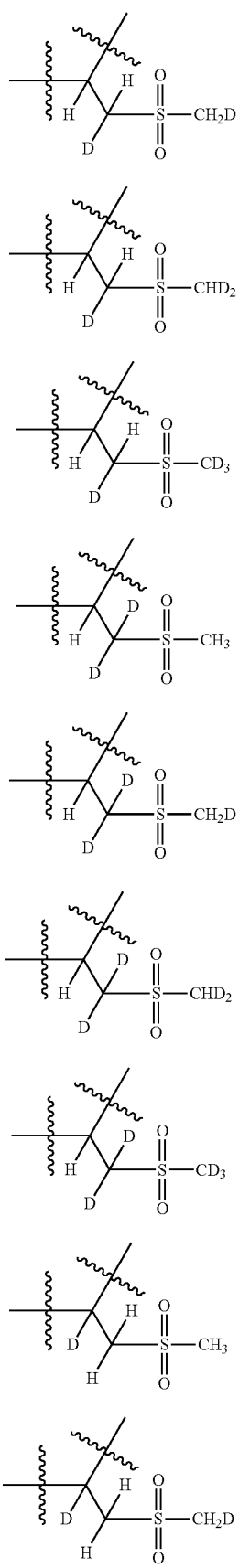
Compound VI-5
Compound VI-6
Compound VI-7
Compound VI-8
Compound VI-9
Compound VI-10
Compound VI-11
Compound VI-12
Compound VI-13
-continued
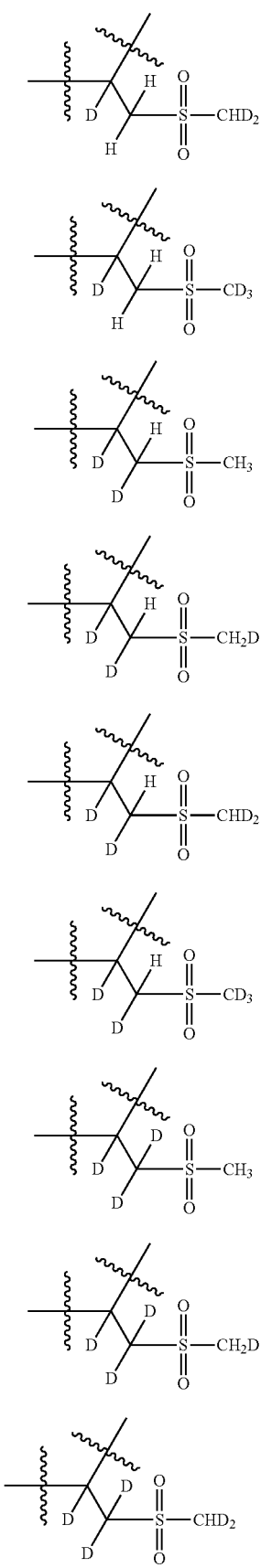
Compound VI-14
Compound VI-15
Compound VI-16
Compound VI-17
Compound VI-18
Compound VI-19
Compound VI-20
Compound VI-21
Compound VI-22
or -continued Compound VI-23

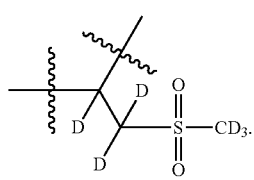

In certain embodiments, one or more hydrogen atoms on the substituents on the phenyl portion of Compound VI are deuterium-enriched. For example, particular compounds provided herein include the following listed compounds, in which the label "D" indicates a deuterium-enriched atomic position, i.e. a sample comprising the given compound has a deuterium enrichment at the indicated position(s) above the natural abundance of deuterium:

Compound VI-24

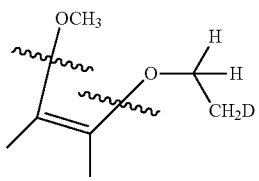

Compound VI-25

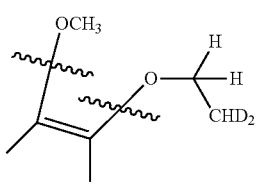

Compound VI-26

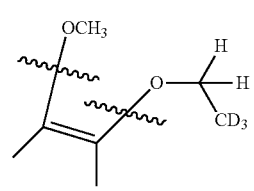

Compound VI-27

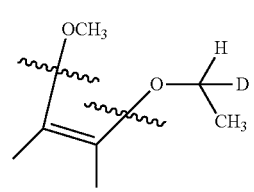

Compound VI-28

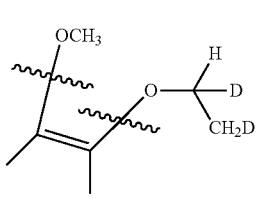

Compound VI-29

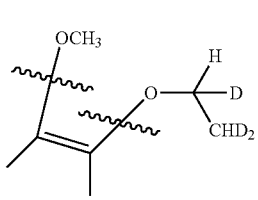

-continued

Compound VI-30

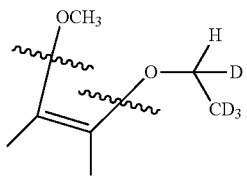

Compound VI-31

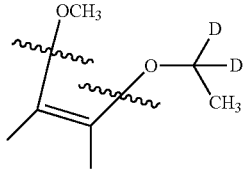

Compound VI-32

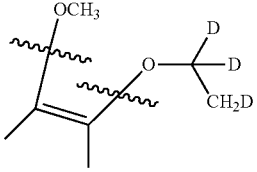

Compound VI-33

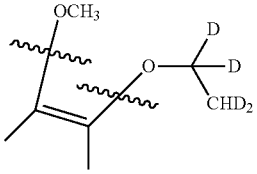

Compound VI-34

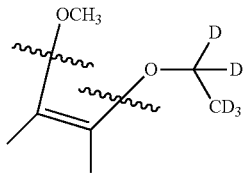

Compound VI-35

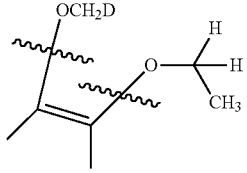

Compound VI-36

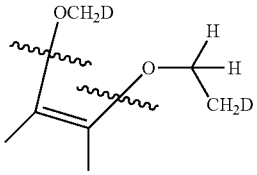

Compound VI-37

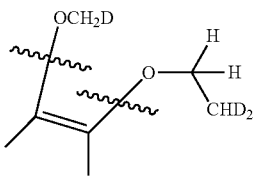

| | |
|---|---|
| 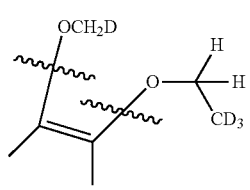 Compound VI-38 | 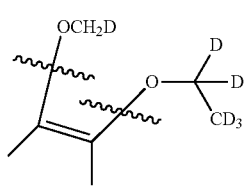 Compound VI-46 |
| 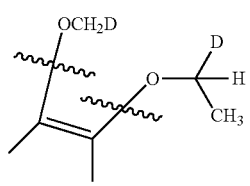 Compound VI-39 | 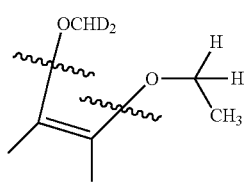 Compound VI-47 |
| 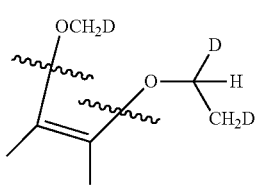 Compound VI-40 | 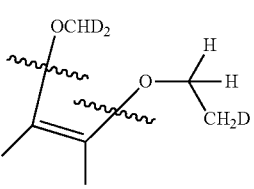 Compound VI-48 |
| 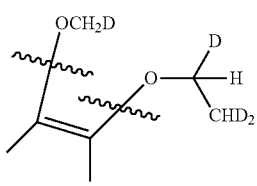 Compound VI-41 | 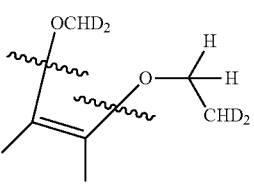 Compound VI-49 |
| 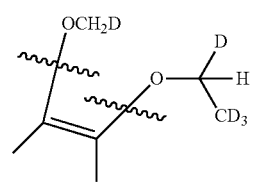 Compound VI-42 | 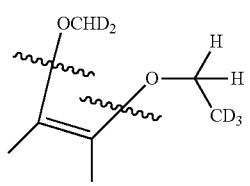 Compound VI-50 |
| 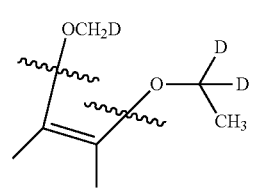 Compound VI-43 | 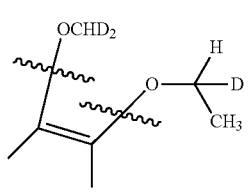 Compound VI-51 |
| 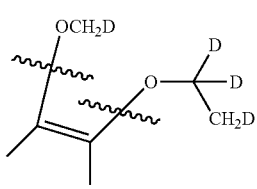 Compound VI-44 | 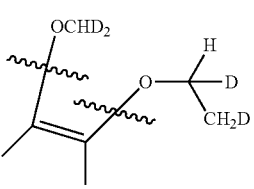 Compound VI-52 |
| 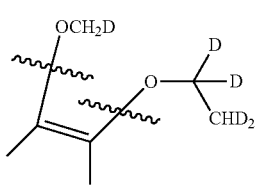 Compound VI-45 | 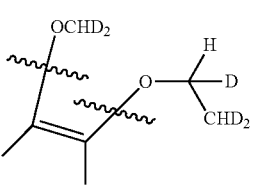 Compound VI-53 |

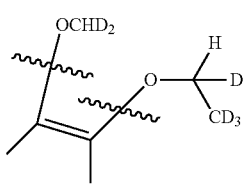
Compound VI-54
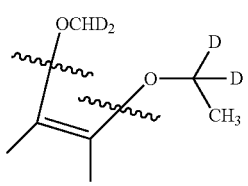
Compound VI-55
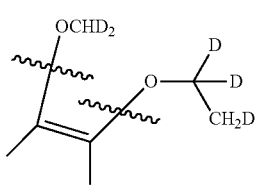
Compound VI-56
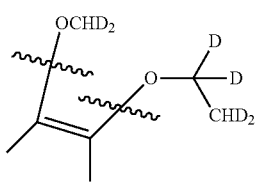
Compound VI-57
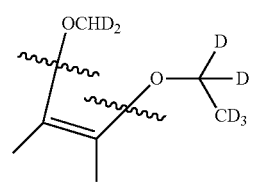
Compound VI-58
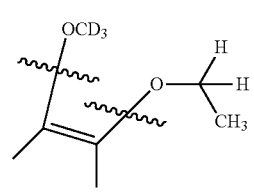
Compound VI-59
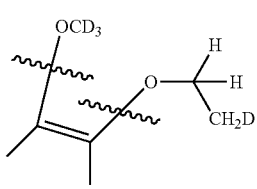
Compound VI-60
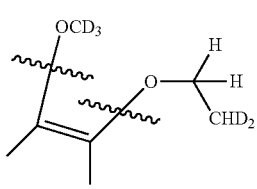
Compound VI-61
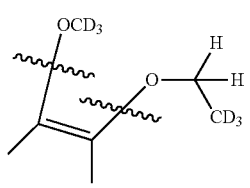
Compound VI-62
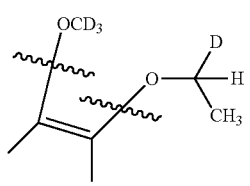
Compound VI-63
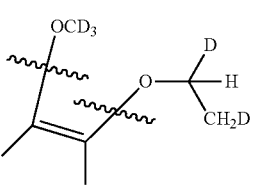
Compound VI-64
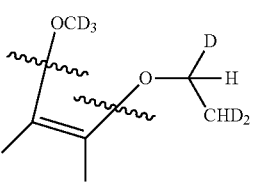
Compound VI-65
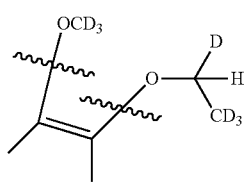
Compound VI-66
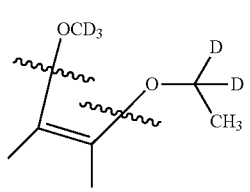
Compound VI-67
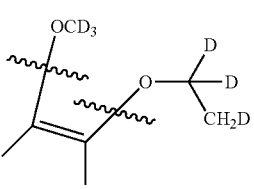
Compound VI-68
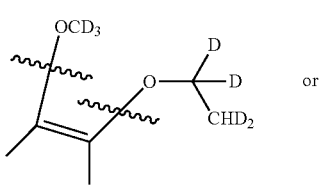
Compound VI-69
or Compound VI-70

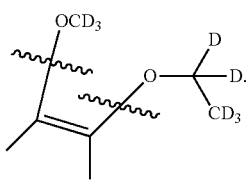

In certain embodiments, one or more hydrogen atoms on the phenyl portion of Compound VI are deuterium-enriched. For example, particular compounds provided herein include, but are not limited to, the following listed compounds, in which the label "D" indicates a deuterium-enriched atomic position, i.e., a sample comprising the given compound has a deuterium enrichment at the indicated position(s) above the natural abundance of deuterium:

Compound VI-71

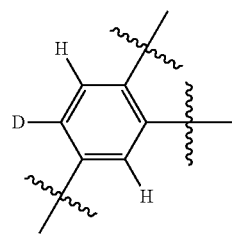

Compound VI-72

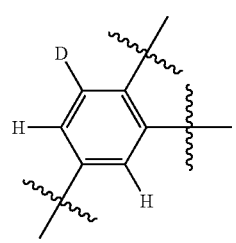

Compound VI-73

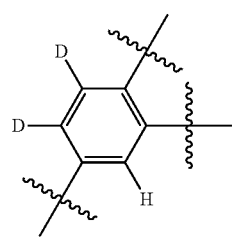

Compound VI-74

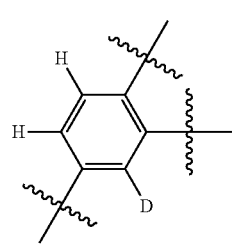

Compound VI-75

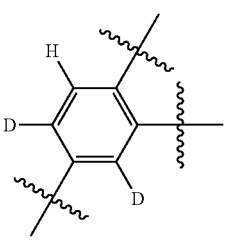

Compound VI-76

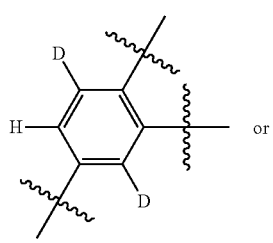

or

Compound VI-77

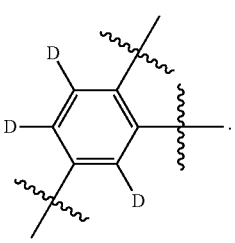

In certain embodiments, one or more hydrogen atoms on the cyclopropyl-carboxamide portion of Compound VI are deuterium-enriched. For example, particular compounds provided herein include, but are not limited to the following listed compounds, in which the label "D" indicates a deuterium-enriched atomic position, i.e., a sample comprising the given compound has a deuterium enrichment at the indicated position(s) above the natural abundance of deuterium:

Compound VI-78

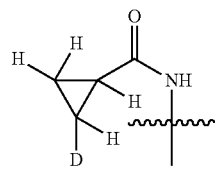

Compound VI-79

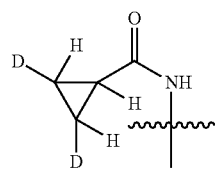

Compound VI-73

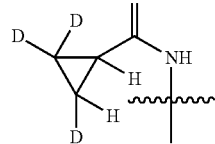

-continued

Compound VI-74
Compound VI-75
Compound VI-76
Cpmound VI-77
Compound VI-78
Compound VI-79
Compound VI-80
Compound VI-81
Compound VI-82

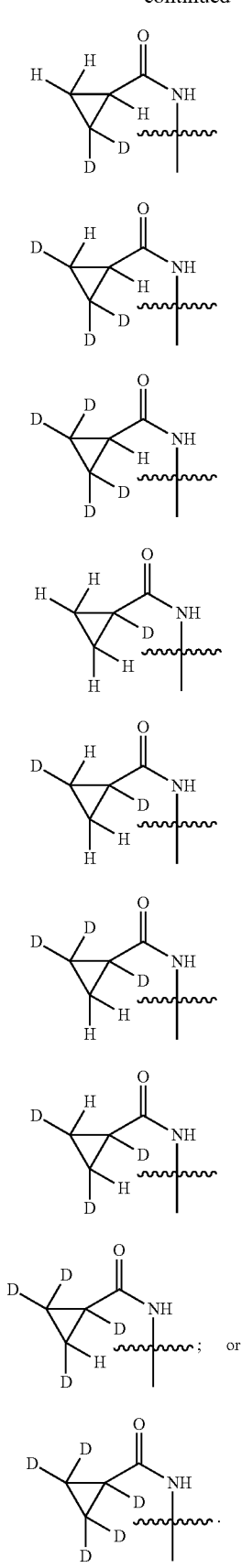

In certain embodiments, one or more hydrogen atoms on the oxoisoindoline portion of Compound VI are deuterium-enriched. For example, particular compounds provided herein include, but are not limited to, the following listed compounds, in which the label "D" indicates a deuterium-enriched atomic position, i.e. a sample comprising the given compound has a deuterium enrichment at the indicated position(s) above the natural abundance of deuterium:

Compound VI-83

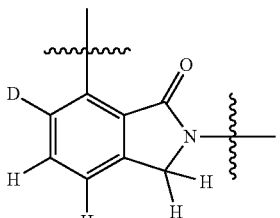

Compound VI-84

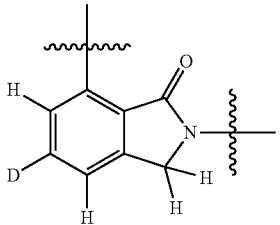

Compound VI-85

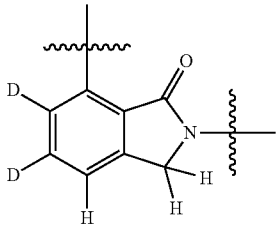

Compound VI-86

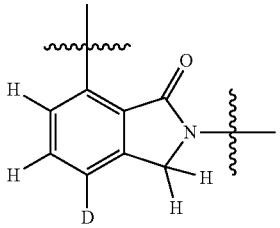

Compound VI-87

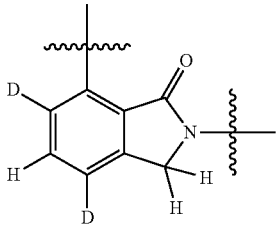

Compound VI-88
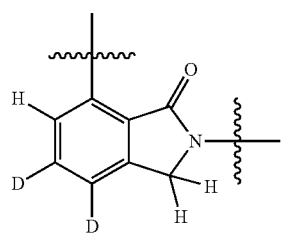
Compound VI-89
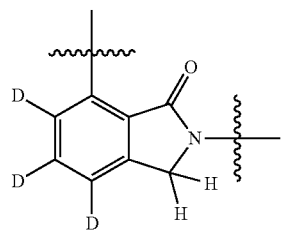
Compound VI-90
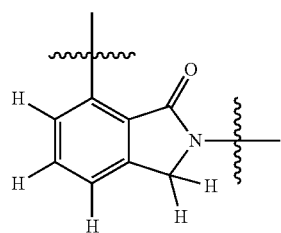
Compound VI-91
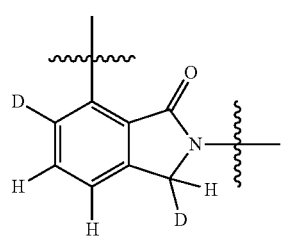
Compound VI-92
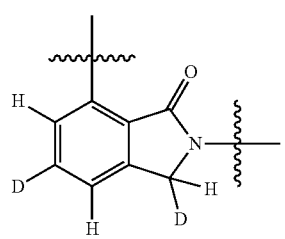
Compound VI-93
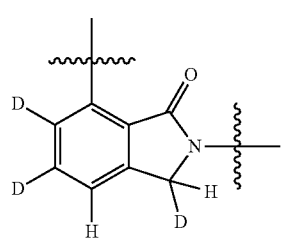
Compound VI-94
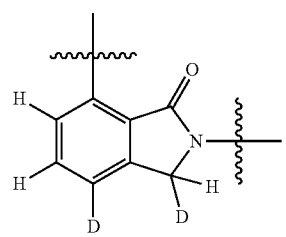
Compound VI-95
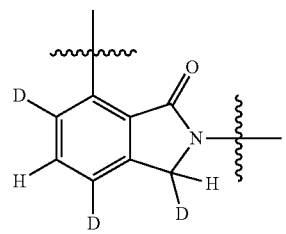
Compound VI-96
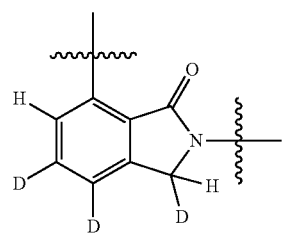
Compound VI-97
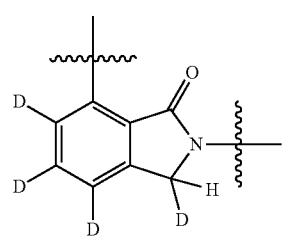
Compound VI-98
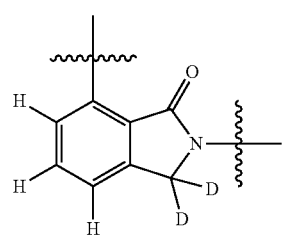
Compound VI-99
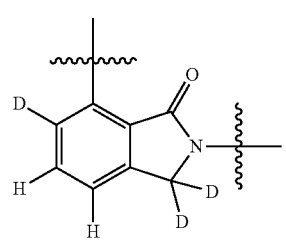

Compound VI-100

Compound VI-101

Compound VI-102

Compound VI-103

Compound VI-104 or

Compound VI-105

In certain embodiments, one or more hydrogen atoms on any of the portions shown above for Compound VI are deuterium-enriched. i.e. any combination of deuteration shown above for Compound VI, is encompassed.

It is understood that one or more deuteriums may exchange with hydrogen under physiological conditions.

In some embodiments, provided herein are carbon-13 isotopologues. In certain embodiments, provided herein are compounds of the following chemical structure:

Compound VII or a stereoisomer thereof,
in which one or more of 1, 2, 3, 4, 5, 6, 7, 8, 9, 10, 11, 12, 13, 14, 15, 16, 17, 19, 19, 20 21, 22 and 23 is/are carbon atom(s) isotopically enriched with carbon-13, and any remaining carbon atom(s) is/are non-enriched carbon atom(s). In particular embodiments, one, two, three, four, five, six, seven, eight, nine, ten, eleven, twelve, thirteen, fourteen, fifteen, sixteen, seventeen, eighteen, nineteen, twenty, twenty-one, twenty-two or twenty-three of carbon atom(s) 1-23 is are/isotopically enriched with carbon-13, and any remaining carbon atom(s) is/are non-enriched.

In some embodiments, provided herein are nitrogen-15 analogues of Compound VI, in which one or more atomic positions of the molecule is isotopically enriched with nitrogen 15. In certain embodiments, provided herein are compounds of the following chemical structure:

Compound VIII or a stereoisomer thereof,
in which one or more of nitrogen atom(s) $N^A$ or $N^B$ is/are isotopically enriched with nitrogen-15, and any remaining nitrogen atom(s) is/are non-enriched nitrogen atom(s). In particular embodiments, one or both of $N^A$ and $N^B$ is/are isotopically enriched with nitrogen-15, and any remaining nitrogen atom(s) is/are non-enriched.

In certain embodiments, $N^A$ is enriched with nitrogen-15. In certain embodiments, $N^B$ is enriched with nitrogen-15. In certain embodiments, $N^A$ and $N^B$ are both enriched with nitrogen-15.

In certain embodiments, one or more hydrogen(s) is/are enriched with deuterium(s) and one or more carbon(s) is/are enriched with carbon-13. In certain embodiments, one or more hydrogen(s) is/are enriched with deuterium and one or more nitrogen(s) is/are enriched with nitrogen-15. In certain embodiments, one or more carbon atom(s) is/are enriched with carbon-13 and one or more nitrogen(s) is/are enriched with nitrogen-5. In certain embodiments, one or more hydrogen(s) is/are enriched with deuterium, one or more carbon(s) are enriched with carbon-13, and one or more nitrogen(s) is/are replaced with nitrogen-15.

In one embodiment, provided herein are isotopologues of (S)-isomer of Compound VI:

Compound IX

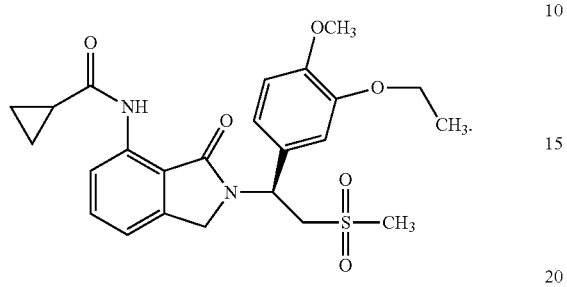

4.2.3 Synthesis

The isotopologues, e.g., the deuterium-, carbon-13-, or nitrogen-15-enriched compounds, described herein may be synthesized using routine synthetic chemistry techniques that are known in the art. Such techniques may involve the use of isotopically-enriched reagents and/or starting materials that are available commercially or readily obtained. In some embodiments, the isotopologues described herein may be synthesized based upon synthetic routes that are known in the art for the corresponding non-isotopically-enriched compounds, wherein one or more of the starting materials, reagents, and/or intermediates of said routes are replaced with an isotopologue of said starting materials, reagents, and/or intermediates. In some embodiments, an isotopologue described herein is synthesized by first synthesizing the compound in its non-isotopically enriched form, and subsequently performing synthetic steps suitable to isotopically enrich the form. In a similar fashion, an isotopologue described herein, which has certain isotopically enriched atoms, may be subjected to synthetic steps suitable to isotopically enrich other atoms of the isotopologue.

In some embodiments, the isotopologues described herein may be synthesized based on the synthetic methods disclosed in U.S. Pat. Nos. 6,020,358 and 6,667,316, and 6,962,940; and U.S. Patent Publication Nos. 2004/0254214 and 2004/0204448, all of which are incorporated herein by reference in their entireties.

In some embodiments, the isoindoline-1,3-dione isotopologues described herein may be synthesized based on the following synthetic route, wherein one or more of the starting materials, reagents, and/or intermediates are replaced with corresponding isotopically-enriched starting materials, reagents, and/or intermediates, and wherein LG is a suitable leaving group and $R^3$ is $C_1$-$C_3$ alkyl or cyclopropyl.

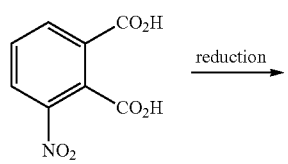

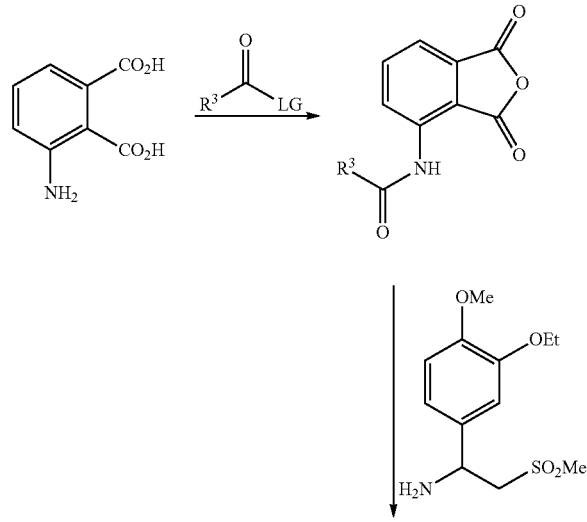

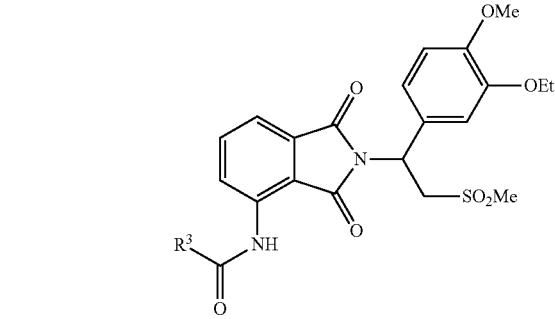

In some embodiments. LG is —C(O)$R^3$ or Cl.

In some embodiments, provided herein are methods of synthesizing isotopically-enriched, e.g., deuterium-, carbon-13-, or nitrogen-15-enriched (S)-2-[1-(3-ethoxy-4-methoxyphenyl)-2-methylsulfonylethyl]-4-acetylaminoisoindoline-1,3-dione. i.e., an isotopologue of compound V:

Compound V

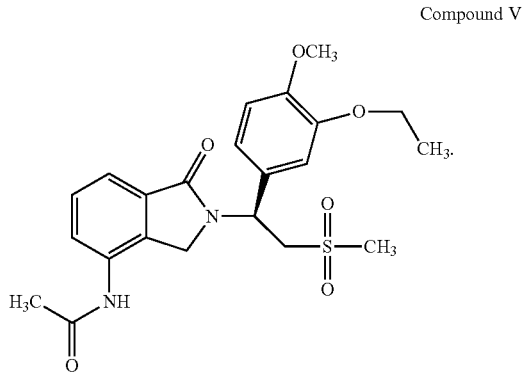 [SMILES: CCOc1cc([C@@H](CS(C)(=O)=O)N2Cc3c(NC(C)=O)cccc3C2=O)ccc1OC]

In some embodiments, an isotopologue of compound V may be synthesized using a synthetic route based on that described in U.S. Pat. No. 6,962,940, which is incorporated herein by reference in its entirety. U.S. Pat. No. 6,962,940 discloses the following synthetic route:

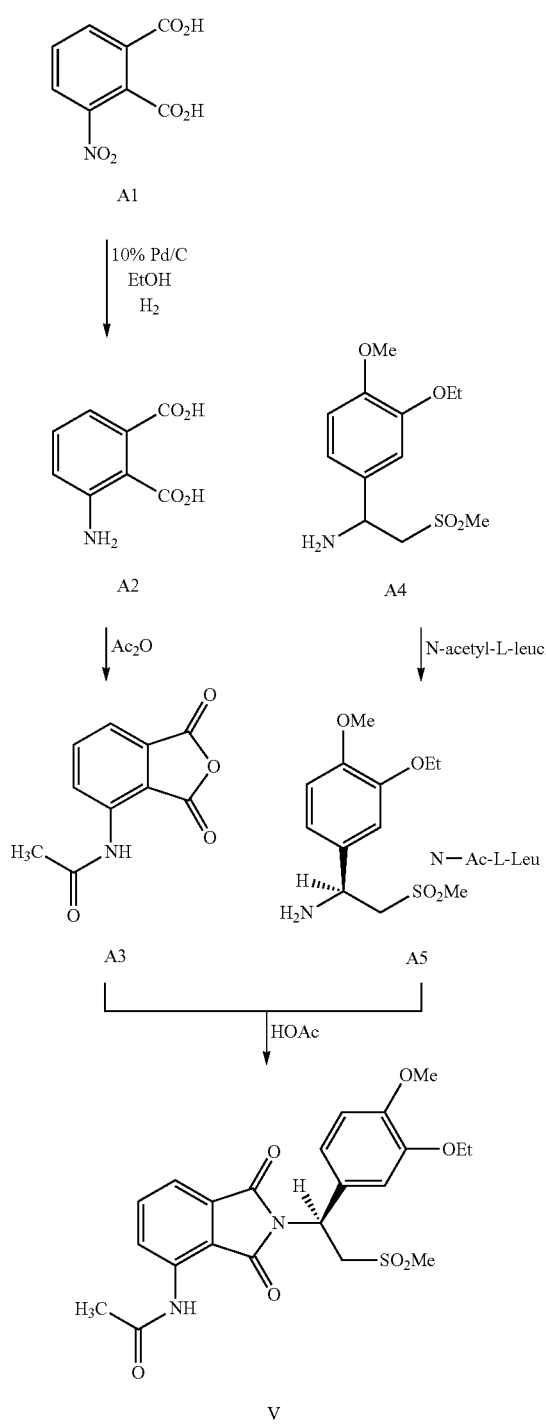

reference in its entirety) is used, which provides a mixture of 3-nitro- and 4-nitro-phthalic acid. In one embodiment, deuterated phthalic acid is treated with concentrated nitric acid at 70° C. 3-nitro-phthalic acid may be separated from 4-nitro-phthalic acid using techniques known in the art. Exemplary separation techniques include those disclosed in U.S. Pat. No. 4,284,797, which is incorporated herein by reference in its entirety.

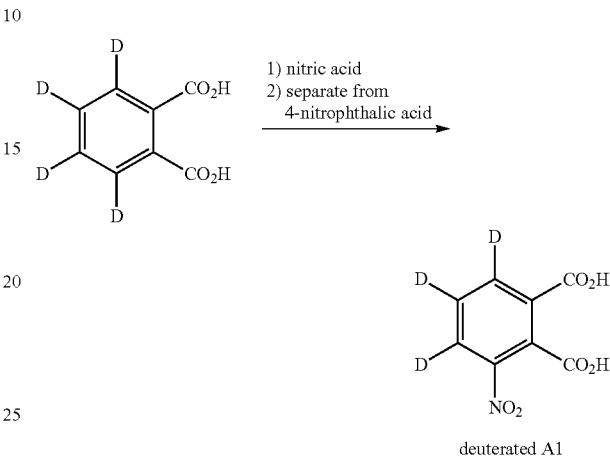

In some embodiments, carbon-13-enriched A1 may be made in similar fashion by replacing deuterated phthalic acid with carbon-13-enriched phthalic acid, which is commercially available.

In some embodiments, the acetamide group of A3 may be enriched with deuterium by reacting A2 with deuterated acetic anhydride, which is commercially available.

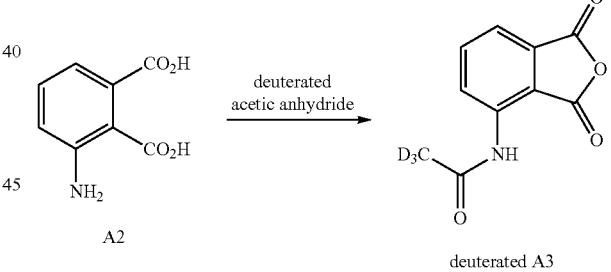

In some embodiments, the acetamide group of A3 may be enriched with carbon-13 in a similar fashion by using carbon-13-enriched acetic anhydride, which is commercially available.

In some embodiments, the aromatic moieties of compound V are deuterated by subjecting compound V to aromatic deuteration conditions, which are known in the art.

N15-enriched compound N15-A1 may be synthesized from phthalic acid. Phthalic acid may be nitrated with $H^{15}NO_3$, which is commercially available, using techniques known in the art (e.g., WO 85/02615) to provide a mixture of 3-($^{15}N$)nitro- and 4-[$^{15}N$]nitro-phthalic acid. 3-[$^{15}N$]nitro-phthalic acid may be separated from 4-[$^{15}N$]nitro-phthalic acid using conventional techniques. Exemplary separation techniques include those disclosed in U.S. Pat. No. 4,284,797. In addition, one could also start with deuterated phthalic acid to get the deuteriums on the aryl ring.

In some embodiments, an isotopologue of compound V is synthesized using the synthetic route illustrated above, wherein one or more of the reagents, starting materials, or intermediates is replaced with corresponding isotopically-enriched starting materials, reagents, or intermediates.

In some embodiments, a deuterium-enriched compound A1 may be synthesized from deuterated phthalic acid, which is commercially available. Specifically, deuterated phthalic acid may be nitrated using techniques known in the art. In one embodiment, the nitration techniques disclosed in International Publication No. WO 85/02615 (incorporated herein by

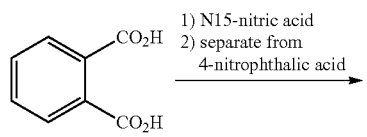

N15-A3 may be synthesized from reduction of N15-A1, followed by acetylation of N15-A2, based upon the synthetic route that described, for example, in U.S. Pat. No. 6,962,940.

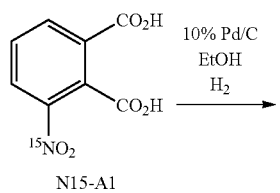

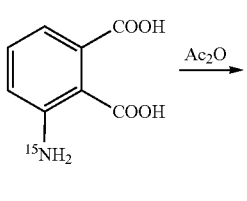 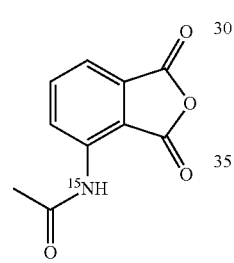

CD3-A3 can be synthesized by the acetylation of A2 with commercially available [$^2H_3$]acetyl anhydride (Acros Organic, 17467) based upon the synthetic route that described, for example, in U.S. Pat. No. 6,962,940.

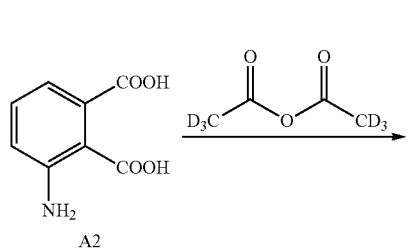

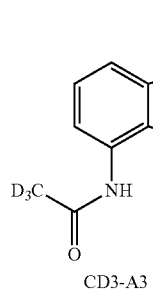

N15 compound V may be synthesized from N15-A3 and A5 based upon the synthetic route that described, for example, in U.S. Pat. No. 6,962,940.

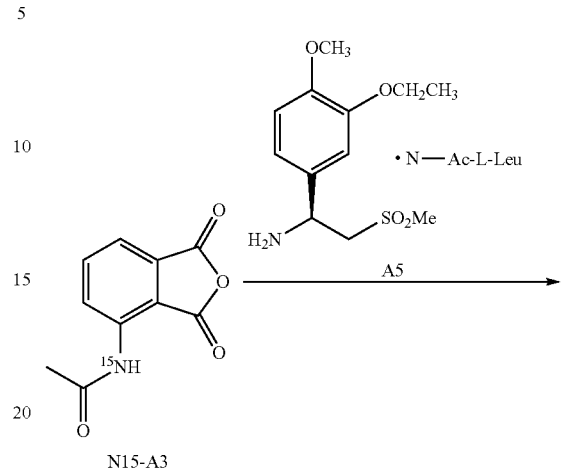

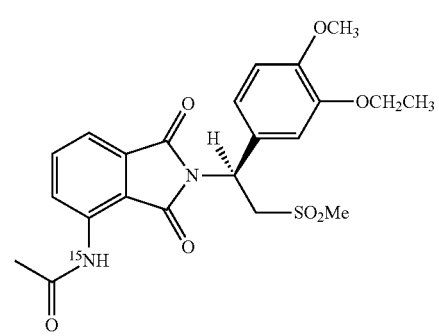

N15 compound V may be synthesized from N15-A3 and N15-A5 based upon the synthetic route that described, for example, in U.S. Pat. No. 6,962,940. Synthesis of N15-A5 is described in more detail herein below.

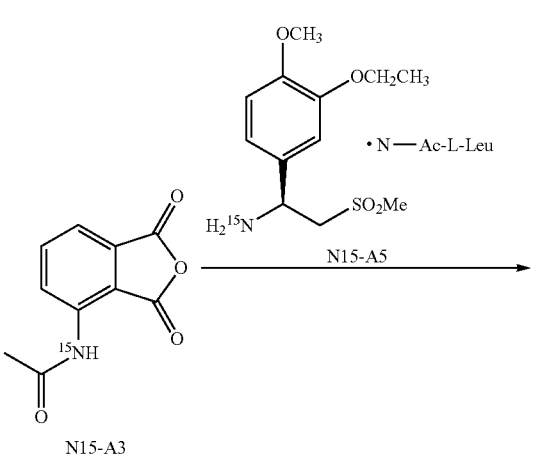

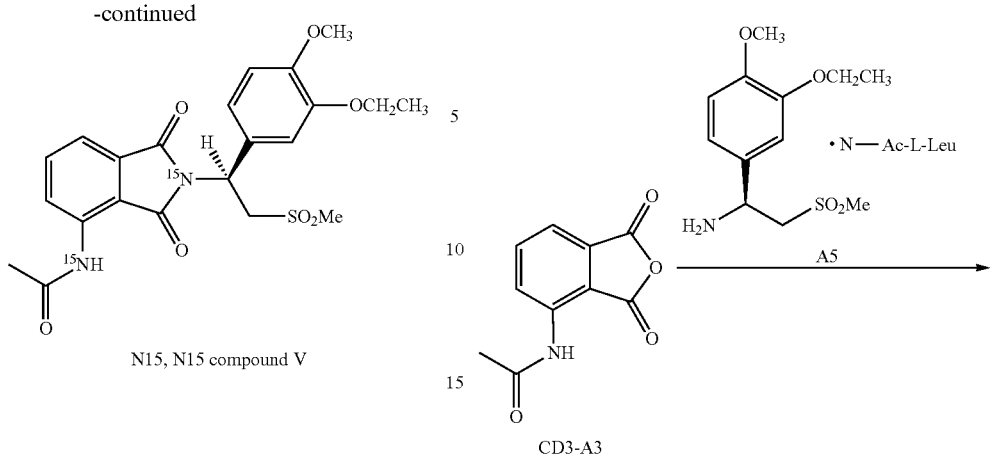

D compound V may be synthesized from A3 and D-A5 based upon the synthetic route that described, for example, in U.S. Pat. No. 6,962,940.

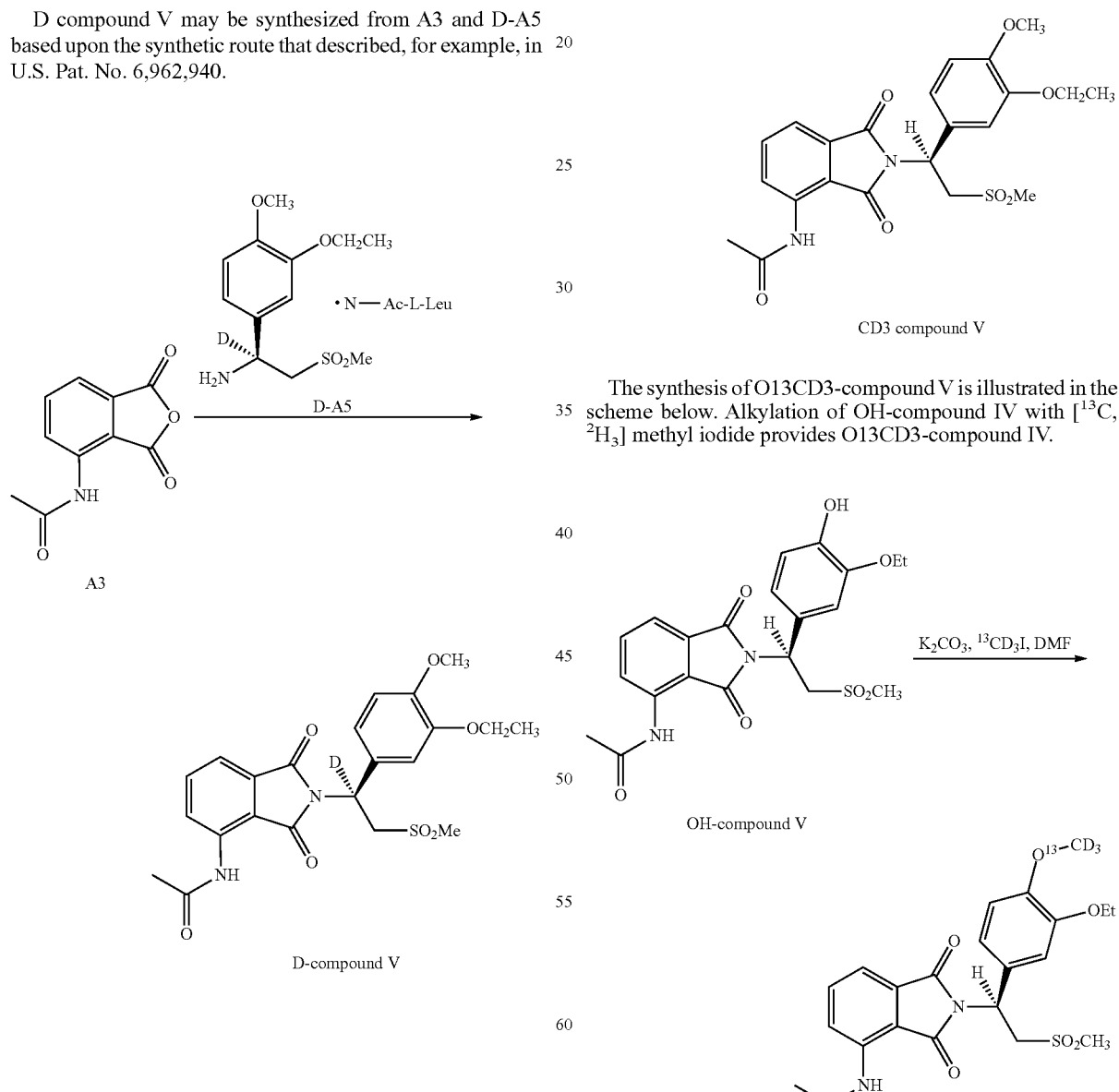

CD3 compound V may be synthesized from CD3-A3 and A5 based upon the synthetic route that described, for example, in U.S. Pat. No. 6,962,940.

The synthesis of O13CD3-compound V is illustrated in the scheme below. Alkylation of OH-compound IV with [$^{13}$C, $^{2}$H$_3$] methyl iodide provides O13CD3-compound IV.

The synthesis of OCD3-compound V is illustrated in the scheme below. Alkylation of OH-compound IV with [²H₃] methyl iodide could provide O13CD3-compound V.

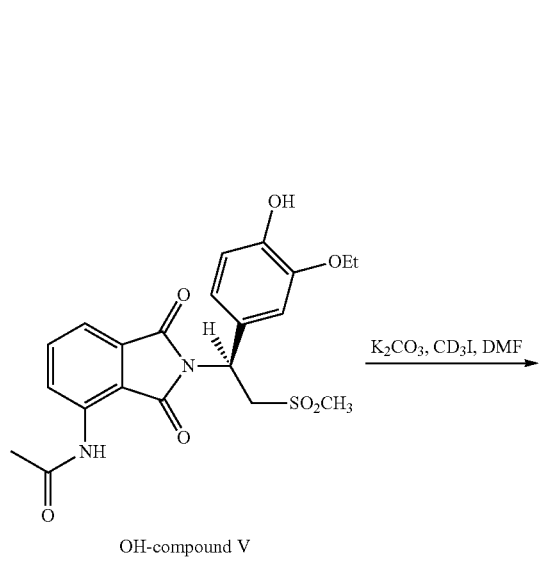

OH-compound V

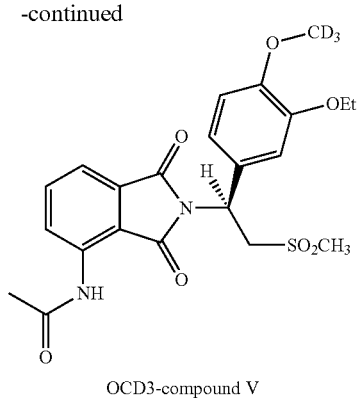

OCD3-compound V

In some embodiments, the isoindoline-1-one isotopologues described herein may be synthesized based on the following synthetic route, wherein at least one of $R^A$ and $R^B$ is an amine protecting group and the other is H; at least one of $R^C$ and $R^D$ is NH₂ and the other is H; and at least one of $R^1$ and $R^2$ is N(H)COR³, wherein $R^3$ is $C_1$-$C_3$ alkyl or cyclopropyl, and the other is H; and wherein one or more of the starting materials, reagents, and/or intermediates are replaced with corresponding isotopically-enriched starting materials, reagents, and/or intermediates.

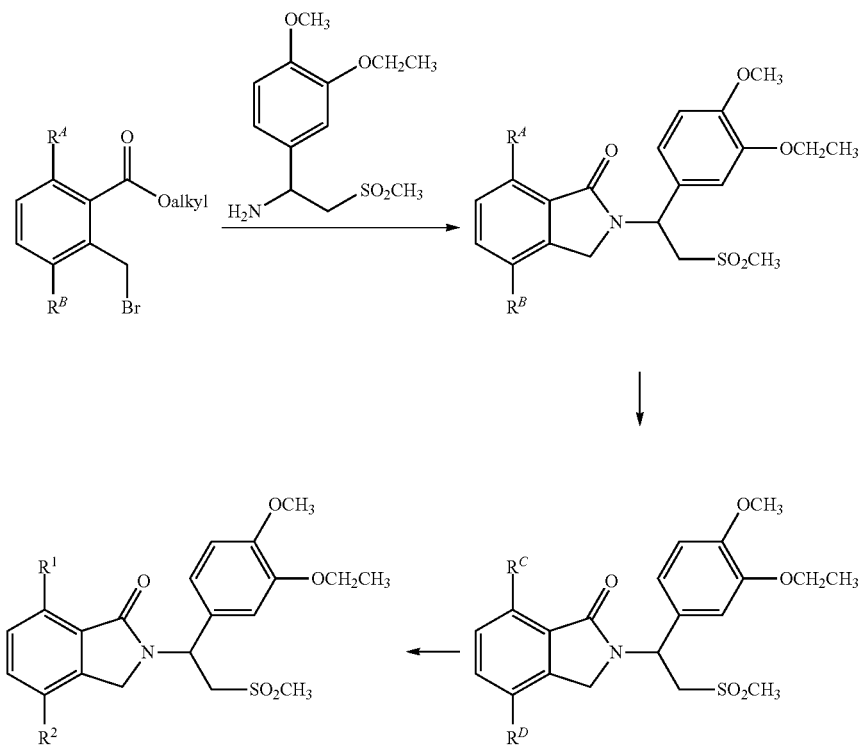

In some embodiments, provided herein are methods of synthesizing isotopically enriched, e.g., deuterium-, carbon-13-, or nitrogen-15 enriched cyclopropyl N-{2-[(1S)-1-(3-ethoxy-4-methoxyphenyl)-2-(methylsulfonyl)ethyl]-3-oxoisoindolin-4-yl}carboxamide. i.e. an isotopologue of compound IX:

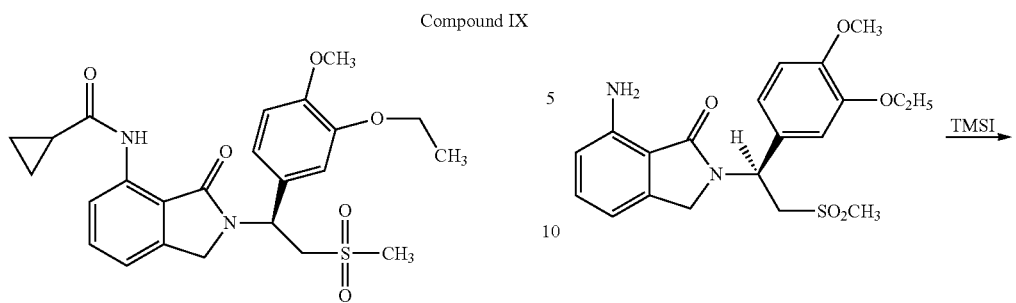

Compound IX

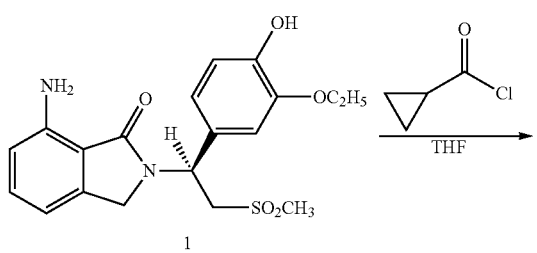

In some embodiments, an isotopologue of compound IX may be synthesized based upon the routes described in U.S. Pat. Nos. 6,667,316 and 6,020,358; and U.S. Patent Publication Nos. 2004/0254214 and 2004/0204448, all of which are incorporated herein by reference in their entireties.

In some embodiments, an isotopologue of compound IX may be synthesized based on the following scheme, wherein one or more reagents, intermediates, or starting materials is replaced with corresponding deuterium-, carbon-13-, or nitrogen-15-enriched reagents, intermediates, or starting materials:

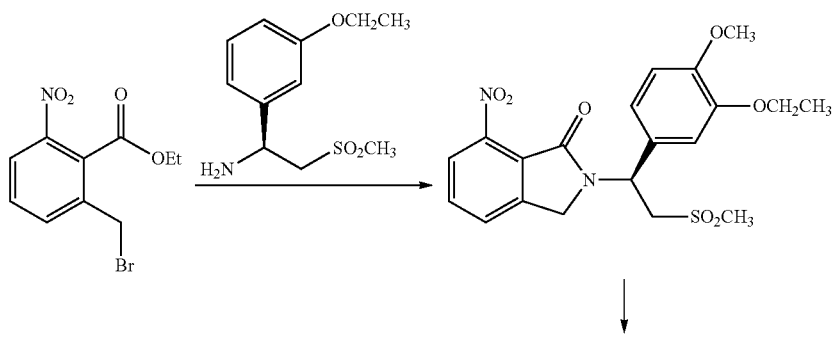

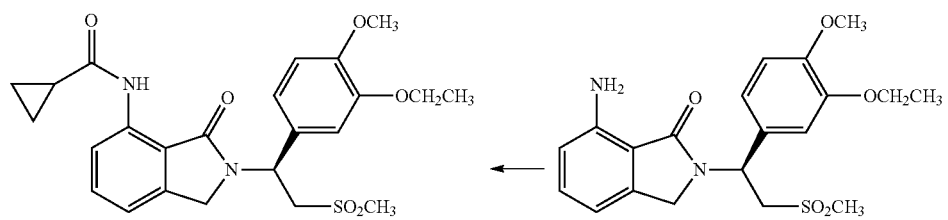

In some embodiments, the aromatic ring moieties of a starting material or intermediate is enriched with deuterium via aromatic deuteration conditions known in the art. In some embodiments, the aromatic moieties of compound IX is deuterated by subjecting compound IX to aromatic deuteration conditions known in the art.

The synthesis of O13CD3-compound-IX is illustrated in the scheme below. Alternatively, O13CD3-compound-IX may be made by reacting $D_3CI$ with 4-hydroxy-3-ethoxybenzonitrile and then transforming the resulting deuterated benzonitrile into the aminosulfone. Similarly, the 3-$CD_3CD_2O$ analog could be prepared from 4-methoxy-3-hydroxybenzonitrile.

-continued

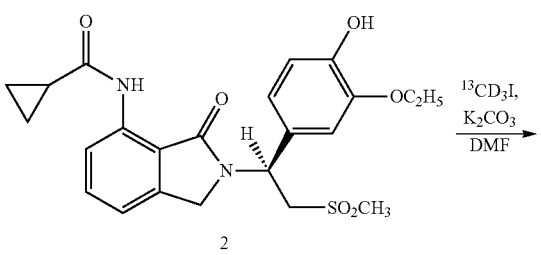

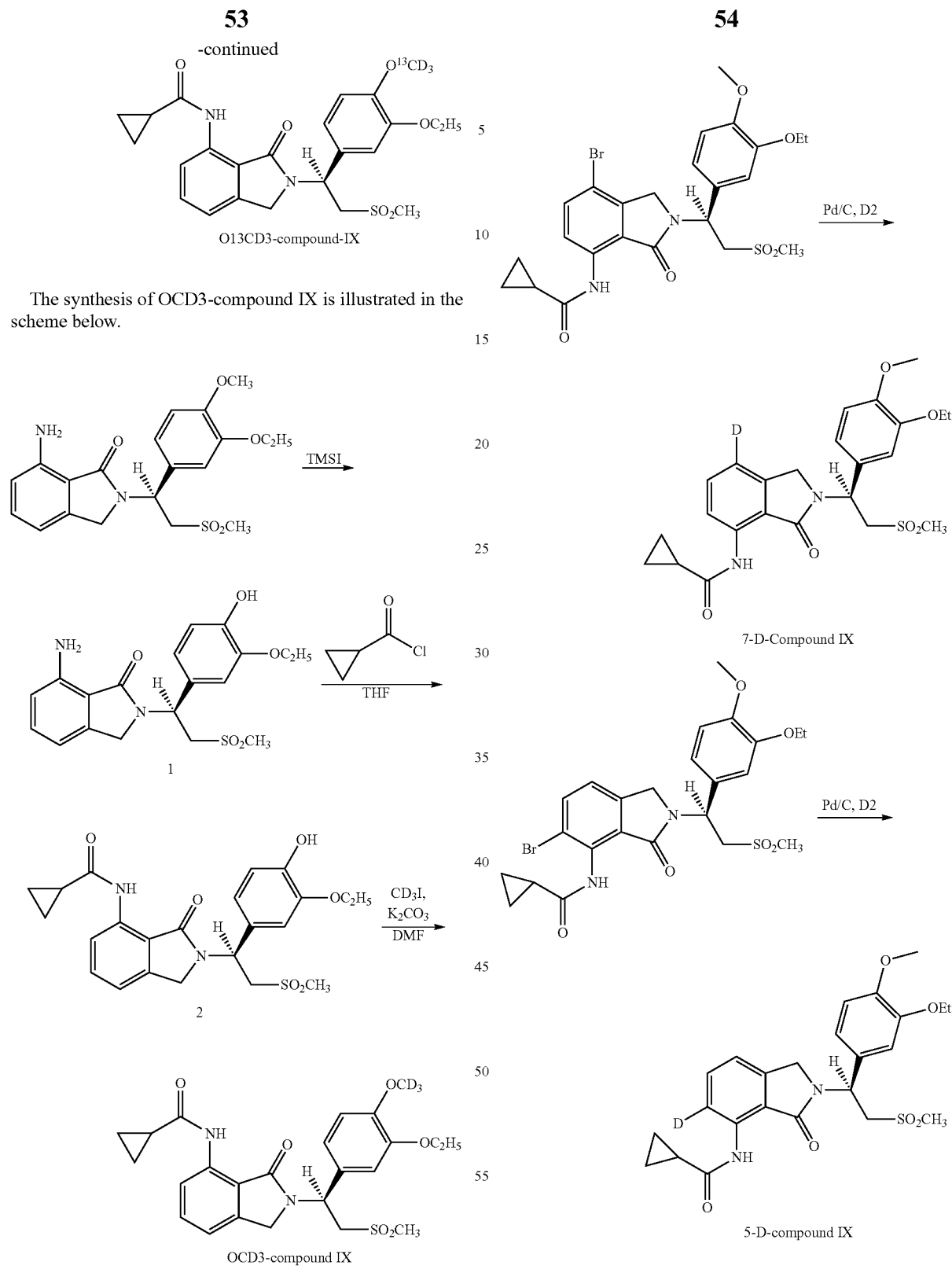

The synthesis of OCD3-compound IX is illustrated in the scheme below.

The synthesis of 5-D and 7-D-compound IX is illustrated in the scheme below. The 7-bromide compound, which is described in US patent publication No. 2004/0254214, is reduced with Pd/C in D2 atmosphere to provide 7-D compound IX. 5-D compound IX could also be made in a similar way.

An isotopologue of compound Da, Db and Dc, which respectively corresponds to D, N15 and C13 derivatives of compound IX, may be synthesized based on the following scheme, wherein one or more reagents, intermediates, or starting materials are replaced with corresponding deuterium-, C13-, or N15-enriched reagents, intermediates, or starting materials.

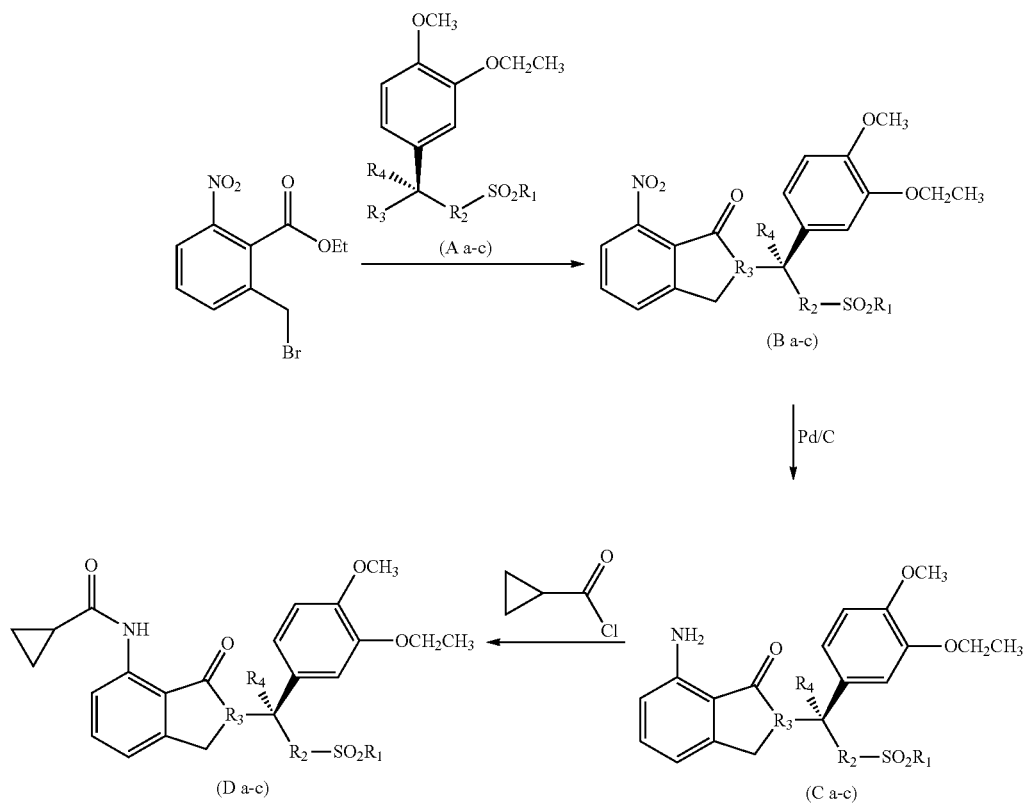

a: R3 = N, R1, R2 = CH3, R4 = D
b: R3 = ¹⁵N, R1, R2 = CH3, R4 = H
c: R3 = N, R1, R2 = ¹³CH3, R4 = H

As shown above, in some embodiments the synthetic routes for making isoindoline-1-one isotopologues and isoindoline-13-dione isotopologues involve the use of 1-(3-ethoxy-4-methoxyphenyl)-2-(methylsulfonyl)ethanamine or its stereoisomer as an intermediate (e.g. A4 and A5). An isotopologue of this intermediate may be used in the described synthetic routes to produce corresponding isoindoline-1-one isotopologues and isoindoline-3-dione isotopologues.

N15-enriched compound A4 may be synthesized based upon the routes described, for example, in U.S. Patent publication No. US2010/0168475. A N15-enriched 3-ethoxy-4-methoxybenzonitrile may be synthesized from 3-ethoxy-4-methoxybenzaldehyde and commercially available N15-enriched hydroxylamine HCl (Alrdich 489743). Reaction of N15-enriched 3-ethoxy-4-methoxybenzonitrile with dimethylsulfone could provide N15-enriched A4 (N15-A4) based upon the routes described, for example, in U.S. Patent publication No. US2010/0168475.

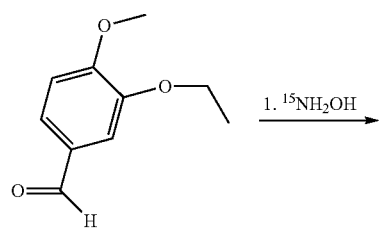

A C13-enriched compound A4 may be synthesized from 3-ethoxy-4-methoxy-benzonitrile and C13-enriched dimethylsulfone based upon the routes described, for example, in U.S. Patent publication No US2010/0168475. The di[¹³C] methylsulfone may be synthesized from oxidation of commercially available di[¹³C]methyl sulfide (Aldrich 658170) to di[¹³C]methyl sulfone using a mixture of potassium permanganate and copper sulfate pentahydrate, based upon the method described, for example, by Shaabani and Lee (*Sulfur Letters* (2003), 26(2), 43-45).

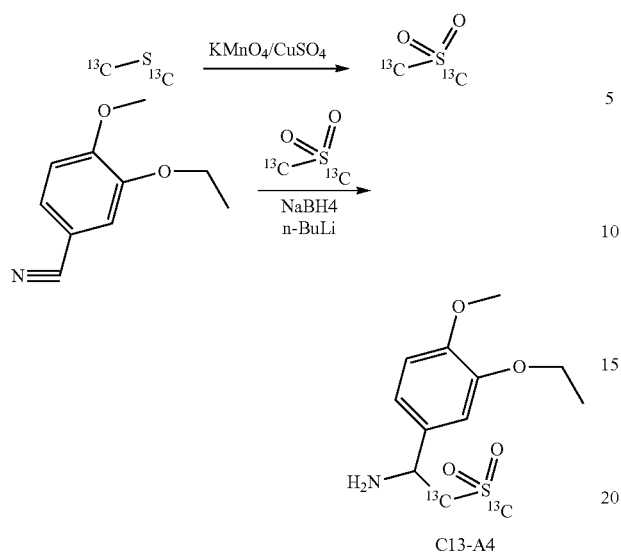

C13-A4

A D-enriched compound A4 (D-A4) may be synthesized from 3-ethoxy-4-methoxy-benzonitrile and dimethylsulfone with NaBD$_4$ (Acros Organic, 19495), based upon the routes described, for example, in U.S. Patent publication No. US2010/0168475.

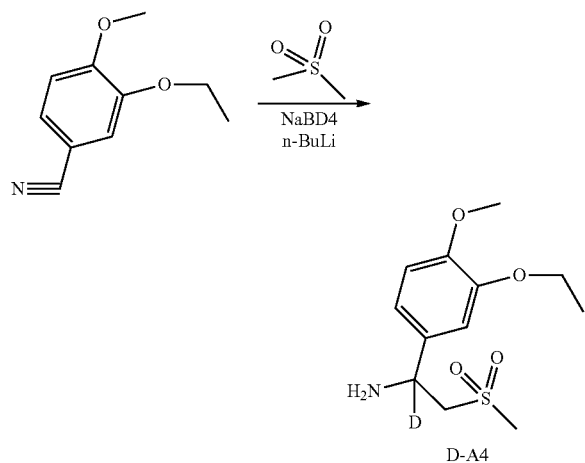

D-A4

N15-enriched compound A4 (N15-A4) may be resolved to yield the S-isomer of N15-A5 using N-acetyl-L-leucine based upon the synthetic route that described, for example, in U.S. Pat. No. 6,962,940.

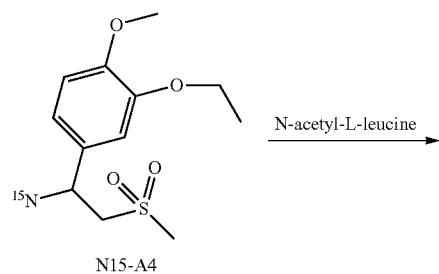

N15-A4

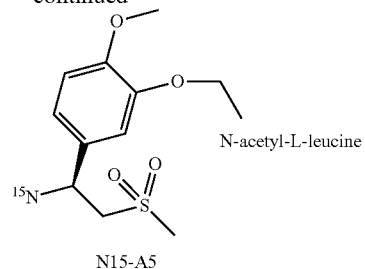

N15-A5

4.3 Methods of Treatment, Prevention and Management

Provided herein are methods of treating, preventing, and/or managing various diseases or disorders using a compound provided herein, or a pharmaceutically acceptable salt, solvate (e.g., hydrate), prodrug, clathrate, or stereoisomer thereof.

In some embodiments, provided herein are methods of treating, managing, and/or preventing diseases or disorders ameliorated by the reduction of levels of TNF-α in a patient which comprise administering to a patient a therapeutically or prophylactically effective amount of a compound provided herein, or a pharmaceutically acceptable prodrug, metabolite, polymorph, salt, solvate, hydrate, or clathrate thereof.

Disorders ameliorated by the inhibition of TNF-α include, but are not limited to: heart disease, such as congestive heart failure, cardiomyopathy, pulmonary edema, endotoxin-mediated septic shock, acute viral myocarditis, cardiac allograft rejection, and myocardial infarction; solid tumors, including but not limited to sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, and retinoblastoma; and blood-born tumors including but not limited to acute lymphoblastic leukemia "ALL", acute lymphoblastic B-cell leukemia, acute lymphoblastic T-cell leukemia, acute myeloblastic leukemia "AML", acute promyelocytic leukemia "APL", acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia "CML", chronic lymphocytic leukemia "CLL", hairy cell leukemia, multiple myeloma and acute and chronic leukemias, for example, lymphoblastic, myelogenous, lymphocytic, and myelocytic leukemias.

Also provided herein is a method of treating, managing or preventing diseases or disorders ameliorated by the inhibition of PDE4 in a patient which comprise administering to a patient a therapeutically or prophylactically effective amount of a compound provided herein, or a pharmaceutically acceptable prodrug, metabolite, polymorph, salt, solvate, hydrate, or clathrate thereof.

Disorders ameliorated by the inhibition of PDE4 include, but are not limited to, asthma inflammation, chronic or acute obstructive pulmonary disease, chronic or acute pulmonary inflammatory disease, inflammatory bowel disease. Crohn's Disease, Bechet's Disease, colitis, ulcerative colitis and arthritis or inflammation due to reperfusion. In a preferred embodiment, the disease or disorder to be treated or prevented is chronic obstructive pulmonary disease.

Other disorders or conditions include, but are not limited to: psoriasis; arthritis including, but not limited to, psoriatic arthritis, osteoarthritis, acute gouty arthritis and rheumatoid arthritis; Lichen Planus; dermatitis including, but not limited to, atopic and contact dermatitis; Behcet's disease; ankylosing spondylitis; rosacca; acne; uveitis; pain; cutaneous lupus; dermatomyositis; sarcoidosis; and Pruigo Nodularis.

In one embodiment, the disorder or condition to be treated, managed, and/or prevented is cancer. In another embodiment, the disorder or condition to be treated, managed, and/or prevented is psoriasis. In another embodiment, the disorder or condition to be treated, managed, and/or prevented is psoriatic arthritis. In another embodiment, the disorder or condition to be treated, managed, and/or prevented is sarcoidosis. In another embodiment, the disorder or condition to be treated, managed, and/or prevented is cutaneous lupus. In another embodiment, the disorder or condition to be treated, managed, and/or prevented is Behcet's disease.

Certain methods provided herein avoid or reduce drug-drug interactions and other adverse effects associated with agents used in the treatment of such disorders. Without being limited by any theory, compounds provided herein may further provide an overall improved therapeutic effectiveness, or therapeutic index, over conventional therapy or over non-isotopologues of compounds described herein. For example, a smaller amount of the drug may in some circumstances be administered to attain the same level of effectiveness.

The magnitude of a prophylactic or therapeutic dose of a particular active ingredient of the invention in the acute or chronic management of a disease or condition will vary, however, with the nature and severity of the disease or condition, and the route by which the active ingredient is administered. The dose and the dose frequency will also vary according to the age, body weight, and response of the individual patient. Suitable dosing regimens can be readily selected by those skilled in the art with due consideration of such factors. In general, the recommended daily dose range for the conditions described herein lie within the range of from about 1 mg to about 1000 mg per day, given as a single once-a-day dose preferably as divided doses throughout a day. In some embodiments, the daily dose is administered twice daily in equally divided doses. In other embodiments, a daily dose range should be from about 5 mg to about 500 mg per day or between about 10 mg and about 200 mg per day. In other embodiments, the daily dose may be administered in 5 mg, 10 mg, 15 mg, 20 mg, 25 mg, 50 mg or 100 mg dosage forms. In managing the patients, the therapy should be initiated at a lower dose, for example, about 1 mg to about 25 mg, and increased if necessary up to about 200 mg to about 1000 mg per day as either a single dose or divided doses, depending on the patients' global response. Alternatively, the daily dose may be from 0.01 mg/kg to 100 mg/kg.

It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

In some embodiments, doses of a compound provided herein, or a pharmaceutically acceptable salt, solvate, clathrate, stereoisomer or prodrug thereof, vary depending on factors such as: specific indication to be treated, prevented, or managed; age and condition of a patient; and amount of second active agent used, if any. In some embodiments, a compound provided herein, or a pharmaceutically acceptable salt, solvate, clathrate, stereoisomer or prodrug thereof, may be used in an amount of from about 0.1 mg to about 500 mg per day, and can be adjusted in a conventional fashion (e.g. the same amount administered each day of the treatment, prevention or management period), in cycles (e.g., one week on, one week off), or in an amount that increases or decreases over the course of treatment, prevention, or management. In other embodiments, the dose can be from about 1 mg to about 300 mg, from about 0.1 mg to about 150 mg, from about 1 mg to about 200 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg.

4.4 Second Active Agents

A compound provided herein, or a pharmaceutically acceptable salt, solvate, prodrug, clathrate, or stereoisomer thereof, can be combined with other pharmacologically active compounds ("second active agents") in methods and compositions provided herein. Certain combinations may work synergistically in the treatment of particular types diseases or disorders, and conditions and symptoms associated with such diseases or disorders. A compound provided herein, or a pharmaceutically acceptable salt, solvate, clathrate, stereoisomer or prodrug thereof, can also work to alleviate adverse effects associated with certain second active agents, and vice versa.

One or more second active ingredients or agents can be used in the methods and compositions provided herein. Second active agents can be large molecules (e.g. proteins) or small molecules (e.g. synthetic inorganic, organometallic, or organic molecules).

Examples of large molecule active agents include, but are not limited to, hematopoietic growth factors, cytokines, and monoclonal and polyclonal antibodies. Specific examples of the active agents are anti-CD40 monoclonal antibodies (such as, for example, SGN-40); histone deacetylase inhibitors (such as, for example, SAHA and LAQ 824); heat-shock protein-90 inhibitors (such as, for example, 17-AAG); insulin-like growth factor-1 receptor kinase inhibitors; vascular endothelial growth factor receptor kinase inhibitors (such as, for example, PTK787); insulin growth factor receptor inhibitors; lysophosphatidic acid acyltransrerase inhibitors; IkB kinase inhibitors; p38MAPK inhibitors; EGFR inhibitors (such as, for example, gefitinib and erlotinib HCL); HER-2 antibodies (such as, for example, trastuzumab (Herceptin®) and pertuzumab (Omnitarg™); VEGFR antibodies (such as, for example, bevacizumab (Avastin™); VEGFR inhibitors (such as, for example, flk-1 specific kinase inhibitors. SU5416 and ptk787/zk222584); P13K inhibitors (such as, for example, wortmannin); C-Met inhibitors (such as, for example, PHA-665752); monoclonal antibodies (such as, for example, rituximab (Rituxan®), tositumomab (Bexxar®), edrecolomab (Panorex®) and G250); and anti-TNF-α antibodies. Examples of small molecule active agents include, but are not limited to, anticancer agents and antibiotics (e.g., clarithromycin).

Specific second active compounds that can be combined with compounds provided herein vary depending on the specific indication to be treated, prevented or managed.

For instance, for the treatment, prevention or management of cancer, second active agents include, but are not limited to: semaxanib; cyclosporin; etanercept; doxycycline; bortezomib; acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other second agents include, but are not limited to: 20-epi-1.25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (Gleevec®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor, leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonatide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin;

nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator, protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; spartosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoictin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoteronc; zeniplatin; zilascorb; and zinostatin stimalamer.

Specific second active agents include, but are not limited to, 2-methoxyestradiol, telomestatin, inducers of apoptosis in multiple myeloma cells (such as, for example, TRAIL), statins, semaxanib, cyclosporin, etanercept, doxycycline, bortezomib, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g. PEG INTRON-A), capecitabine, cisplatin, thiotepa, fludarabine, carboplatin, liposomal daunorubicin, cytarabine, doxetaxol, pacilitaxel, vinblastine, IL-2. GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

In certain embodiments, examples of second active agents include, but are not limited to conventional therapeutics used to treat or prevent pain such as antidepressants, anticonvulsants, antihypertensives, anxiolytics, calcium channel blockers, muscle relaxants, non-narcotic analgesics, opioid analgesics, anti-inflammatories, cox-2 inhibitors, immunomodulatory agents, alpha-adrenergic receptor agonists or antagonists, immunosuppressive agents, corticosteroids, hyperbaric oxygen, ketamine, other anesthetic agents, NMDA antagonists, and other therapeutics found, for example, in the *Physician's Desk Reference* 2003. Specific examples include, but are not limited to salicylic acid acetate (Aspirin®), celecoxib (Celebrex®), Enbrel®, ketamine, gabapentin (Neurontin®), phenyloin (Dilantin®), carbamazepine (Tegretol®), oxcarbazepine (Trileptal®), valproic acid (Depakene®), morphine sulfate, hydromorphone, prednisone, griseofulvin, penthonium, alendronate, dyphenhydramide, guanethidine, ketorolac (Acular®), thyrocalcitonin, dimethylsulfoxide (DMSO), clonidine (Catapress®), bretylium, ketanserin, reserpine, droperidol, atropine, phentolamine, bupivacaine, lidocaine, acetaminophen, nortriptyline (Pamelor®), amitriptyline (Elavil®), imipramine (Tofranil®), doxepin (Sinequan®), clomipramine (Anafranil®), fluoxetine (Prozac®), sertraline (Zoloft®), naproxen, nefazodone (Serzone®), venlafaxine (Effexor®), trazodone (Desyrel®), bupropion (Wellbutrin®), mexiletine, nifedipine, propranolol, tramadol, lamotrigine, vioxx, ziconotide, ketamine, dextromethorphan, benzodiazepines, baclofen, tizanidine and phenoxybenzamine.

In other embodiments, examples of second active agents include, but are not limited to a steroid, a light sensitizer, an integrin, an antioxidant, an interferon, a xanthine derivative, a growth hormone, a neutrotrophic factor, a regulator of neovascularization, an anti-VEGF antibody, a prostaglandin, an antibiotic, a phytoestrogen, an anti-inflammatory compound or an antiangiogenesis compound, or a combination thereof. Specific examples include, but are not limited to verteporfin, purlytin, an angiostatic steroid, rhuFab, interferon-2α, pentoxifylline, tin etiopurpurin, motexafin, lucentis, lutetium, 9-fluoro-11,21-dihydroxy-16,17-1-methylethylidenebis(oxy)pregna-1,4-diene-3,20-dione, latanoprost (see U.S. Pat. No. 6,225,348), tetracycline and its derivatives, rifamycin and its derivatives, macrolides, metronidazole (U.S. Pat. Nos. 6,218,369 and 6,015,803), genistein, genistin, 6'-O-Mal genistin, 6'-O-Ac genistin, daidzein, daidzin, 6'-O-Mal daidzin, 6'-O-Ac daidzin, glycitein, glycitin, 6'-O-Mal glycitin, biochanin A, formononetin (U.S. Pat. No. 6,001,368), triamcinolone acetomide, dexamethasone (U.S. Pat. No. 5,770,589), thalidomide, glutathione (U.S. Pat. No. 5,632,984), basic fibroblast growth factor (bFGF), transforming growth factor b (TGF-b), brain-derived neurotrophic factor (BDNF), plasminogen activator factor type 2 (PAI-2), EYE101 (Eyetech Pharmaceuticals), LY333531 (Eli Lilly), Miravant, and RETISERT implant (Bausch & Lomb). All of the references cited herein are incorporated in their entireties by reference.

In other embodiments, examples of second active agents include, but are not limited to, keratolytics, retinoids, α-hydroxy acids, antibiotics, collagen, botulinum toxin, interferon, steroids, and immunomodulatory agents. Specific examples include, but are not limited to, 5-fluorouracil, masoprocol, trichloroacetic acid, salicylic acid, lactic acid, ammonium lactate, urea, tretinoin, isotretinoin, antibiotics, collagen, botulinum toxin, interferon, corticosteroid, transretinoic acid and collagens such as human placental collagen, animal placental collagen, Dermalogen, AlloDerm, Fascia, Cymetra, Autologen, Zyderm, Zyplast, Resoplast, and Isolagen.

In other embodiments, examples of second active agents include, but are not limited to anticoagulants, diuretics, cardiac glycosides, calcium channel blockers, vasodilators, prostacyclin analogues, endothelin antagonists, phosphodiesterase inhibitors (e.g. PDE V inhibitors), endopeptidase inhibitors, lipid lowering agents, thromboxane inhibitors, and other therapeutics known to reduce pulmonary artery pressure. Specific examples include, but are not limited to, warfarin (Coumadin®), a diuretic, a cardiac glycoside, digoxin-oxygen, diltiazem, nifedipine, a vasodilator such as prostacyclin (e.g., prostaglandin 12 (PG2), epoprostenol (EPO, Floran®), treprostinil (Remodulin®), nitric oxide (NO), bosentan (Tracleer®), amlodipine, epoprostenol (Floran®), treprostinil (Remodulin®), prostacyclin, tadalafil (Cialis®), simvastatin (Zocor®), omapatrilat (Vanlev®), irbesartan (Avapro®), pravastatin (Pravachol®), digoxin, L-arginine, iloprost, betaprost, and sildenafil (Viagra®).

In other embodiments, examples of second active agents include, but are not limited to, anthracycline, platinum, alkylating agent, oblimersen (Genasense®), cisplatinum, cyclophosphamide, temodar, carboplatin, procarbazine, gliadel, tamoxifen, topotecan, methotrexate, taxotere, irinotecan, capecitabine, cisplatin, thiotepa, fludarabine, carboplatin, liposomal daunorubicin, cytarabine, doxetaxol, paclitaxel, vinblastine. IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, bleomycin, hyaluronidase, mitomycin C, mepacrine, thiotepa, tetracycline and gemcitabine.

In other embodiments, examples of second active agents include, but are not limited to, chloroquine, quinine, quinidine, pyrimethamine, sulfadiazine, doxycycline, clindamycin, metloquine, halofantrine, primaquine, hydroxychloroquine, proguanil, atovaquone, azithromycin, suramin, pentamidine, melarsoprol, nifurtimox, benznidazole, amphotericin B, pentavalent antimony compounds (e.g., sodium stiboglucuronate), interfereon gamma, itraconazole, a combination of dead promastigotes and BCG, leucovorin, corticosteroids, sulfonamide, spiramycin, IgG (serology), trimethoprim, and sulfamethoxazole.

In other embodiments, examples of second active agents include, but are not limited to; antibiotics (therapeutic or prophylactic) such as, but not limited to, ampicillin, tetracycline, penicillin, cephalosporins, streptomycin, kanamycin, and erythromycin; antivirals such as, but not limited to amantadine, rimantadine, acyclovir, and ribavirin; immunoglobulin; plasma; immunologic enhancing drugs such as, but not limited to, levami sole and isoprinosine biologics such as, but not limited to, gammaglobulin, transfer factor, interleukins, and interferons; hormones such as, but not limited to thymic; and other immunologic agents such as, but not limited to, B cell stimulators (e.g. BAFF/BlyS), cytokines (e.g. IL-2, IL-4, and IL-5), growth factors (e.g. TGF-α), antibodies (e.g., anti-CD40 and IgM), oligonucleotides containing unmethylated CpG motifs, and vaccines (e.g., viral and tumor peptide vaccines).

In other embodiments, examples of second active agents include, but are not limited to: opioids; a dopamine agonist or antagonist, such as, but not limited to, Levodopa, L-DOPA, cocaine, α-methyl-tyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate. Sinemet CR, and Symmetrel; a MAO inhibitor, such as, but not limited to iproniazid, clorgyline, phenelzine and isocarboxazid; a COMT inhibitor, such as, but not limited to, tolcapone and entacapone; a cholinesterase inhibitor, such as, but not limited to, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, and demecarium; an anti-inflammatory agent, such as, but not limited to naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, Rho-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone or betamethasone and other glucocorticoids; and an antiemetic agent, such as, but not limited to metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and a mixture thereof.

In other embodiments, examples of second active agents include, but are not limited to immunomodulatory agents, immunosuppressive agents, antihypertensives, anticonvulsants, fibrinolytic agents, antiplatelet agents, antipsychotics, antidepressants, benzodiazepines, buspirone, amantadine, and other known or conventional agents used in patients with CNS injury/damage and related syndromes. Specific examples include, but are not limited to: steroids (e.g., glucocorticoids, such as, but not limited to methylprednisolone, dexamethasone and betamethasone); an anti-inflammatory agent, including, but not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone; a cAMP analog including, but not limited to db-cAMP; an agent comprising a methylphenidate drug, which comprises 1-threo-methylphenidate, d-threo-methylphenidate, dl-threo-methylphenidate, 1-erythro-methylphenidate, d-erythro-methylphenidate, dl-erythro-methylphenidate, and a mixture thereof; and a diuretic agent such as, but not limited to mannitol, furosemide, glycerol, and urea.

In other embodiments, examples of second active agent include, but are not limited to a tricyclic antidepressant agent, a selective serotonin reuptake inhibitor, an antiepileptic agent (gabapentin, pregabalin, carbamazepine, oxcarbazepine, levitiracetam, topiramate), an antiaryhthmic agent, a sodium channel blocking agent, a selective inflammatory mediator inhibitor, an opioid agent, a second immunomodulatory compound, a combination agent, and other known or conventional agents used in sleep therapy. Specific examples include, but are not limited to, Neurontin, oxycontin, morphine, topiramate, amitryptiline, nortryptiline, carbamazepine, Levodopa, L-DOPA, cocaine, α-methyl-tyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate. Sinemet CR, Symmetrel, iproniazid, clorgyline, phenelzine, isocarboxazid, tolcapone, entacapone, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, demecarium, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts. RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone, benzbromarone, betamethasone and other glucocorticoids, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and a mixture thereof.

In other embodiments, examples of second active agents include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; and G-CSF; hydroxyurea; butyrates or butyrate derivatives; nitrous oxide; hydroxy urea; HEMOXIN™ (NIPRISAN™; see U.S. Pat. No. 5,800,819); Gardos channel antagonists such as clotrimazole and triaryl methane derivatives; Deferoxamine; protein C; and transfusions of blood, or of a blood substitute such as Hemospan™ or Hemospan™ PS (Sangart).

In one embodiment, the second active agent is prednisone. In another embodiment, the second active agent is Aspirins®. In another embodiment, the second active agent is clarithromycin. In another embodiment, the second active agent is bortezomib. In another embodiment, the second active agent is dexamethasone.

Administration of a compound provided herein, or a pharmaceutically acceptable salt, solvate, clathrate, stereoisomer or prodrug thereof, and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. One of administration for compounds provided herein is oral. Routes of administration for the second active agents or ingredients are known to those of ordinary skill in the art. See, e.g. *Physicians' Desk Reference* ($60^{th}$ ed. 2006).

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount(s) of compounds provided herein and any optional additional active agents concurrently administered to the patient.

As discussed elsewhere herein, also encompassed is a method of reducing, treating and/or preventing adverse or undesired effects associated with conventional therapy including, but not limited to, surgery, chemotherapy, radiation therapy, hormonal therapy, biological therapy and immunotherapy. Compounds provided herein and other active ingredients can be administered to a patient prior to, during, or after the occurrence of the adverse effect associated with conventional therapy.

4.5 Cycling Therapy

In certain embodiments, the prophylactic or therapeutic agents provided herein are cyclically administered to a patient. Cycling therapy involves the administration of an active agent for a period of time, followed by a rest (i.e. discontinuation of the administration) for a period of time, and repeating this sequential administration. Cycling therapy can reduce the development of resistance to one or more of the therapies, avoid or reduce the side effects of one of the therapies, and/or improve the efficacy of the treatment.

Consequently, in one embodiment, a compound provided herein is administered daily in a single or divided doses in a four to six week cycle with a rest period of about a week or two weeks. Cycling therapy further allows the frequency, number, and length of dosing cycles to be increased. Thus, another embodiment encompasses the administration of a compound provided herein for more cycles than are typical when it is administered alone. In yet another embodiment, a compound provided herein is administered for a greater number of cycles than would typically cause dose-limiting toxicity in a patient to whom a second active ingredient is not also being administered.

In one embodiment, a compound provided herein is administered daily and continuously for three or four weeks at a dose of from about 0.1 mg to about 500 mg per day, followed by a rest of one or two weeks. In other embodiments, the dose can be from about 1 mg to about 300 mg, from about 0.1 mg to about 150 mg, from about 1 mg to about 200 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg, followed by a rest.

In one embodiment, a compound provided herein and a second active ingredient are administered orally, with administration of the compound provided herein occurring 30 to 60 minutes prior to the second active ingredient, during a cycle of four to six weeks. In another embodiment, the combination of a compound provided herein and a second active ingredient is administered by intravenous infusion over about 90 minutes every cycle.

Typically, the number of cycles during which the combination treatment is administered to a patient will be from about one to about 24 cycles, from about two to about 16 cycles, or from about four to about three cycles.

4.6 Pharmaceutical Compositions and Dosage Forms

Pharmaceutical compositions can be used in the preparation of individual, single unit dosage forms. Pharmaceutical compositions and dosage forms provided herein comprise a compound provided herein, or a pharmaceutically acceptable salt, solvate, stereoisomer, clathrate, or prodrug thereof. Pharmaceutical compositions and dosage forms can further comprise one or more excipients.

Pharmaceutical compositions and dosage forms provided herein can also comprise one or more additional active ingredients. Examples of optional second, or additional, active ingredients are disclosed in Section 4.4, above.

Single unit dosage forms provided herein are suitable for oral, mucosal (e.g. nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g. nasal sprays or inhalers); gels; liquid dosage forms suitable for oral or mucosal administration to a patient, including suspensions (e.g. aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms are used will vary from one another will be readily apparent to those skilled in the art. See, e.g., *Remington's Pharmaceutical Sciences*. 18th ed. Mack Publishing. Easton Pa. (1990).

In one embodiment, pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided are pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions can comprise excipients that are well known in the art and are listed, for example, in the *U.S. Pharmacopeia* (USP) 25-NF20 (2002). In general, lactose-free compositions comprise active ingredients, a binder/filler, and a lubricant in pharmaceutically compatible and pharmaceutically acceptable amounts. In one embodiment, lactose-free dosage forms comprise active ingredients, microcrystalline cellulose, pre-gelatinized starch, and magnesium stearate.

Also provided are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice*. 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are, in one embodiment, packaged using materials known to prevent exposure to water such that they can be included in suitable formulary kits. Examples of suitable packaging include, but are not limited to hermetically sealed foils, plastics, unit dose containers (e.g. vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to the route by which it is to be administered to patients. In one embodiment, dosage forms comprise a compound provided herein in an amount of from about 0.10 to about 500 mg. In other embodiments, dosage forms comprise a compound provided herein in an amount of about 0.1, 1, 25, 7.5, 10, 12.5, 15, 17.5, 20, 25, 50, 100, 150, 200, 250, 300, 350, 400, 450, or 500 mg.

In other embodiments, dosage forms comprise the second active ingredient in an amount of 1 to about 1000 mg, from about 5 to about 500 mg, from about 10 to about 350 mg, or from about 50 to about 200 mg. Of course, the specific amount of the second active agent will depend on the specific agent used, the diseases or disorders being treated or managed, and the amount(s) of a compound provided herein, and any optional additional active agents concurrently administered to the patient.

4.6.1 Oral Dosage Forms

Pharmaceutical compositions that are suitable for oral administration can be provided as discrete dosage forms, such as, but not limited to, tablets (e.g., chewable tablets), caplets, capsules, and liquids (e.g. flavored syrups). Such dosage forms contain predetermined amounts of active ingredients, and may be prepared by methods of pharmacy well known to those skilled in the art. See generally, *Remington's Pharmaceutical Sciences*, 18th ed. Mack Publishing, Easton Pa. (1990).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to water, glycols, oils, alcohols, flavoring agents, preservatives, and coloring agents. Examples of excipients suitable for use in solid oral dosage forms (e.g., powders, tablets, capsules, and caplets) include, but are not limited to starches, sugars, micro-crystalline cellulose, diluents, granulating agents, lubricants, binders, and disintegrating agents.

In one embodiment, oral dosage forms are tablets or capsules, in which case solid excipients are employed. In another embodiment, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation. American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms provided herein include, but are not limited to talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or tiller in pharmaceutical compositions is, in one embodiment, present in from about 50 to about 99 weight percent of the pharmaceutical composition or dosage form.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In one embodiment, pharmaceutical compositions comprise from about 0.5 to about 15 weight percent of disintegrant, or from about 1 to about 5 weight percent of disintegrant.

Disintegrants that can be used in pharmaceutical compositions and dosage forms include, but are not limited to agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Piano, Tex.). CAB-O-SIL (a pyrogenic silicon dioxide product sold by Cabot Co. of Boston, Mass.), and mixtures thereof. If used at all, lubricants may be used in an amount of less than about 1 weight percent of the pharmaceutical compositions or dosage forms into which they are incorporated.

In one embodiment, a solid oral dosage form comprises a compound provided herein, anhydrous lactose, microcrystalline cellulose, polyvinylpyrrolidone, stearic acid, colloidal anhydrous silica, and gelatin.

4.6.2 Controlled Release Dosage Forms

Active ingredients provided herein can be administered by controlled release means or by delivery devices that are well known to those of ordinary skill in the art. Examples include, but are not limited to those described in U.S. Pat. Nos. 3,845, 770; 3,916,899; 3,536,809; 3,598,123, and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active agents provided herein. In one embodiment, provided are single unit dosage forms suitable for oral administration such as, but not limited to tablets, capsules, gelcaps, and caplets that are adapted for controlled-release.

In one embodiment, controlled-release pharmaceutical products improve drug therapy over that achieved by their non-controlled counterparts. In another embodiment, the use of a controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

In another embodiment, the controlled-release formulations are designed to initially release an amount of drug (active ingredient) that promptly produces the desired therapeutic or prophylactic effect, and gradually and continually release of other amounts of drug to maintain this level of therapeutic or prophylactic effect over an extended period of time. In one embodiment, in order to maintain a constant level of drug in the body, the drug can be released from the dosage form at a rate that will replace the amount of drug being metabolized and excreted from the body. Controlled-release of an active ingredient can be stimulated by various conditions including, but not limited to pH, temperature, enzymes, water, or other physiological conditions or compounds.

4.6.3 Parenteral Dosage Forms

Parenteral dosage forms can be administered to patients by various mutes including, but not limited to, subcutaneous, intravenous (including bolus injection), intramuscular, and intraarterial. In some embodiments, administration of a parenteral dosage form bypasses patients' natural defenses against contaminants, and thus, in these embodiments, parenteral dosage forms are sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms. For example, cyclodextrin and its derivatives can be used to increase the solubility of a compound provided herein. See, e.g., U.S. Pat. No. 5,134,127, which is incorporated herein by reference.

4.6.4 Topical and Mucosal Dosage Forms

Topical and mucosal dosage forms provided herein include, but are not limited to, sprays, aerosols, solutions, emulsions, suspensions, eye drops or other ophthalmic preparations, or other forms known to one of skill in the art. See, e.g., *Remington's Pharmaceutical Sciences.* 16th and 18th eds., Mack Publishing. Easton Pa. (1980 & 1990); and *Introduction to Pharmaceutical Dosage Forms,* 4th ed., Lea & Febiger, Philadelphia (1985). Dosage forms suitable for treating mucosal tissues within the oral cavity can be formulated as mouthwashes or as oral gels.

Suitable excipients (e.g. carriers and diluents) and other materials that can be used to provide topical and mucosal dosage forms encompassed herein are well known to those skilled in the pharmaceutical arts, and depend on the particular tissue to which a given pharmaceutical composition or dosage form will be applied. In one embodiment, excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms. Examples of additional ingredients are well known in the art. See, e.g. *Remington's Pharmaceutical Sciences,* 16th and 18th eds., Mack Publishing, Easton Pa. (1980 & 1990).

The pH of a pharmaceutical composition or dosage form may also be adjusted to improve delivery of one or more active ingredients. Also, the polarity of a solvent carrier, its ionic strength, or tonicity can be adjusted to improve delivery. Compounds such as stearates can also be added to pharmaceutical compositions or dosage forms to alter the hydrophilicity or lipophilicity of one or more active ingredients so as to improve delivery. In other embodiments, stearates can serve as a lipid vehicle for the formulation, as an emulsifying agent or surfactant, or as a delivery-enhancing or penetration-enhancing agent. In other embodiments, salts, solvates, prodrugs, clathrates, or stereoisomers of the active ingredients can be used to further adjust the properties of the resulting composition.

4.7 Kits

In one embodiment, active ingredients provided herein are not administered to a patient at the same time or by the same route of administration. In another embodiment, provided are kits which can simplify the administration of appropriate amounts of active ingredients.

In one embodiment, a kit comprises a dosage form of a compound provided herein. Kits can further comprise additional active ingredients such as oblimersen (Genasense®), melphalan, G-CSF, GM-CSF, EPO, topotecan, dacarbazine, irinotecan, taxotere. IFN, COX-2 inhibitor, pentoxifylline, ciprofloxacin, dexamethasone, IL2, IL8, IL18, Ara-C, vinorelbine, isotretinoin, 13 cis-retinoic acid, or a pharmacologically active mutant or derivative thereof, or a combination thereof. Examples of the additional active ingredients include, but are not limited to, those disclosed herein (see, e.g., section 4.3).

In other embodiments, kits can further comprise devices that are used to administer the active ingredients. Examples of such devices include, but are not limited to, syringes, drip bags, patches, and inhalers.

Kits can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

5. EXAMPLES

Isotopically enriched analogs of the compounds provided herein may generally be prepared according synthetic routes known in the art, wherein one or more of the reagents, starting materials, precursors, or intermediates used is replaced by one or more isotopically enriched reagents, starting materials, precursors, or intermediates. Isotopically enriched reagents, starting materials, precursors, or intermediates are commercially available or may be prepared by routine procedures known to one of skill in the art.

5.1 (S)-N-(2-(1-(3-Ethoxy-4-([$^{13}$C,$^{2}$H$_3$]Methoxy)-Phenyl)-2-(Methylsulfonyl)Ethyl)-3-Oxoisoindolin-4-Yl)Cyclopropanecarboxamide

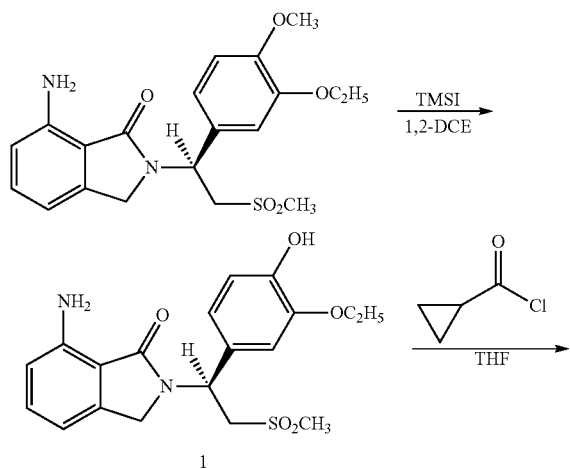

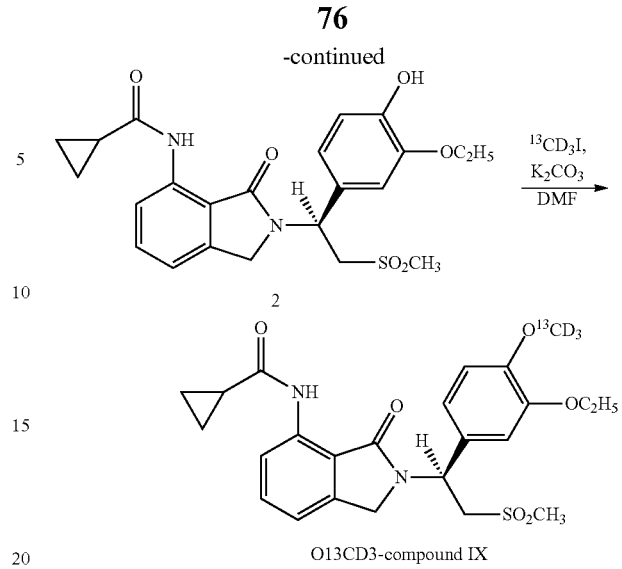

O13CD3-compound IX

Step 1: A mixture of (S)-7-amino-2-(1-(3-ethoxy-4-methoxyphenyl)-2-(methylsulfonyl)ethyl)isoindolin-1-one (10 g, 24.7 mmol) and TMSI (50 g, 250 mmol) was heated to 80° C. for 2 hours. The mixture was cooled to 0° C. in an ice-water bath. To the mixture, was added 5% aqueous sodium sulfide solution. The mixture was stirred at room temperature until all solid dissolved. The mixture was extracted with methylene chloride. The organic layer was washed with brine. The solvent was removed in vacuo to give a foam. The crude mixture was purified by column chromatography (silica gel. MeOH/CH$_2$Cl$_2$) to give (S)-7-amino-2-(1-(3-ethoxy-4-hydroxyphenyl)-2-(methylsulfonyl)ethyl)isoindolin-1-one (6 g), which was used in the next step without further purification.

Step 2: To a solution of (S)-7-amino-2-(1-(3-ethoxy-4-hydroxyphenyl)-2-(methylsulfonyl)ethyl)isoindolin-1-one (5.86 g, 15 mmol) in THF (60 mL), was added cyclopropane carbonyl chloride (1.5 mL, 16 mmol). The mixture was heated to 60° C. for 1 hour. The solvent was removed in vacuo. The crude mixture was purified by column chromatography, then prep HPLC, to give (S)-N-(2-(1-(3-ethoxy-4-hydroxyphenyl)-2-(methylsulfonylethyl)-3-oxoisoindolin-4-yl)cyclopropanecarboxamide as a white solid (1.38 g): mp: 295.8° C.

Step 3: A mixture of (S)-N-(2-(1-(3-ethoxy-4-hydroxyphenyl)-2-(methylsulfonyl)ethyl)-3-oxoisoindolin-4-yl)cyclopropanecarboxamide (1.0 g, 2.18 mmol), K$_2$CO$_3$ (362 mg, 2.62 mmol) and [$^{13}$C,$^{2}$H$_3$]methyl iodide (0.2 mL, 2.62 mmol) in DMF (10 mL) was heated at 40° C. After 18 hours, the mixture was allowed to cool to room temperature. To the mixture, was added K$_2$CO$_3$ (362 mg, 2.62 mmol) and [$^{13}$C, $^{2}$H$_3$]methyl iodide (0.2 mL, 2.62 mmol). After 4 hours, water (80 mL) was added to the mixture. The suspension was filtered and washed with water. The crude mixture was purified by column chromatography (Silca gel. MeOH/CH2Cl2) and recrystallized from ethanol to give (S)-N-(2-(1-(3-ethoxy-4-([$^{13}$C,$^{2}$H$_3$]methoxy)-phenyl)-2-(methylsulfonyl)ethyl)-3-oxoisoindolin-4-yl)cyclopropanecarboxamide as a solid (760 mg, 73% yield): mp: 172° C.; $^1$H NMR (300 MHz, DMSO-d$_6$) δ 0.89 (d, J=6.0 Hz, 4H), 1.33 (t, J=7.0 Hz, 3H), 1.80 (quin, J=6.1 Hz, 1H), 3.03 (s, 3H), 3.89-4.22 (m, 4H), 4.32 (dd, J=10.5, 14.6 Hz, 1H), 4.65 (d, J=17.9 Hz, 1H), 5.88 (dd, J=4.2, 10.4 Hz, 1H) 6.96 (s, 2H), 7.04 (s, 1H), 7.19 (d, J=7.6 Hz, 1H), 7.50 (t, J=7.8 Hz, 1H), 8.23 (d, J=8.1 Hz, 1H), 10.50 (s, 1H); $^{13}$C NMR (DMSO-d$_6$) δ 7.77, 14.67, 15.43, 40.94, 46.19, 48.89, 54.64 (CD$_3$, J$_{CD}$=22 Hz), 63.88, 111.89, 111.95, 112.22, 116.87, 117.00, 117.49, 119, 78, 129.92, 132.92, 136.99, 142.21, 148.03, 148.84, 168.12, 171.71.

5.2 (S)-N-(2-(1-(3-Ethoxy-4-([$^{13}$C,$^{2}$H$_3$]Methoxy)-Phenyl)-2-(Methylsulfonyl)Ethyl)-1-Dioxoisoindo-lin-4-Yl)Acetamide

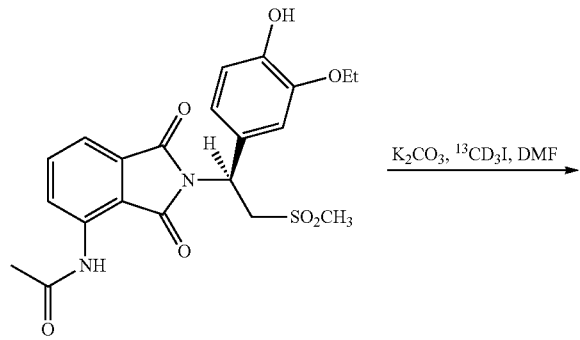

A mixture of (S)-N-(2-(1-(3-ethoxy-4-hydroxyphenyl)-2-(methylsulfonyl)ethyl)-1,3-dioxoisoindolin-4-yl)acetamide (3.0 g, 6.73 mmol), K$_2$CO$_3$ (1.1 g, 8.07 mmol) and [$^{13}$C,$^{2}$H$_3$] methyl iodide (0.5 mL, 8.07 mmol) in DMF (30 mL) was heated at 40° C. After 18 hours, the mixture was allowed to cool to room temperature. To the mixture, was added water (80 mL). The suspension was filtered and washed with water. The crude mixture was purified by column chromatography (Silica gel. MeOH/CH2Cl2) and recrystallized from ethanol to give (S)-N-(2-(1-(3-ethoxy-4-([$^{13}$C,$^{2}$H$_3$]methoxy)-phenyl)-2-(methylsulfonyl)ethyl)-1,3-dioxoisoindolin-4-yl)acetamide as a solid (2.0 g, 65% yield): mp, 154° C.; $^1$H NMR (300 MHz, DMSO-d$_6$) δ 1.33 (t, J=6.9 Hz, 3H), 2.20 (s, 3H), 3.03 (s, 3H), 4.02 (q, J=7.0 Hz, 2H), 4.10-4.22 (m, J=4.2, 14.4 Hz, 1H), 4.27-4.45 (m, J=10.4, 14.5 Hz, 1H), 5.79 (dd, J=4.2, 10.5 Hz, 1H), 6.89-7.02 (m, 2H), 7.08 (d, J=1.7 Hz, 1H), 7.57 (d, J=7.0 Hz, 1H), 7.79 (t, J=7.8 Hz, 1H), 8.45 (d, J=8.3 Hz, 1H), 9.71 (s, 1H); $^{13}$C NMR (75 MHz, DMSO-d$_6$) δ 14.64, 24.16, 41.03, 47.16, 52.87, 54.65 (CD$_3$, J$_{CD}$=22.0 Hz), 63.87, 111.72, 111.79, 112.39, 116.66, 118.18, 119.71, 126.08, 129.42, 131.33, 135.90, 136.49, 147.88, 148.93, 166.91, 167.81, 169.23.

5.3 Preparation of Intermediates

5.3.1 Deuterated 3-nitrophthalic acid

Deuterated 3-nitrophthalic acid may be synthesized based on the procedures described in International Publication No. WO 85/02615 and U.S. Pat. No. 4,284,797, both of which are incorporated herein by reference in their entireties. Specifically, 100 parts by weight of 99% by weight concentrated nitric acid is added to a reaction vessel and is brought to a temperature of about 70° C. To the solution is added 10 parts by weight of commercially available deuterated phthalic acid. Nitration is allowed to continue at about 70° C. for about three hours, which provides a mixture of deuterated 3-nitro- and 4-nitro-phthalic acid. This mixture is suspended in methyl ethyl ketone. Water is then added, and the temperature is raised to 40° C. 30% sodium hydroxide is then added to bring the pH value of the mixture to 1.2. The aqueous crystal mass is then separated, and the organic solution is returned to the reaction apparatus. The reaction is heated again to 40° C. and sodium hydrogen carbonate is added portionwise with thorough stirring. After CO$_2$ evolution subsides and the pH reaches 2.8, the mono-sodium salt of 3-nitrophthalic acid will precipitate in crystalline form. The mixture is cooled to 5° C. and the salt is filtered off and dried to provide the mono-sodium salt of deuterated 3-nitrophthalic acid. This mono-sodium salt is then treated with acid to obtain deuterated 3-nitrophthalic acid.

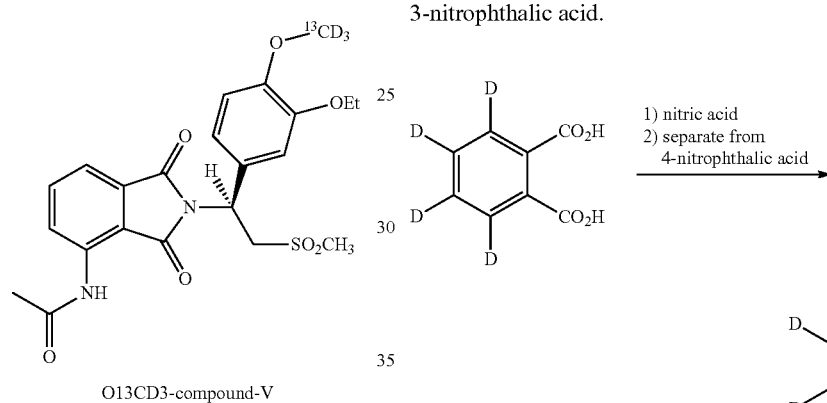

deuterated A1

5.3.2 3-[$^{15}$N]Nitrophthalic acid

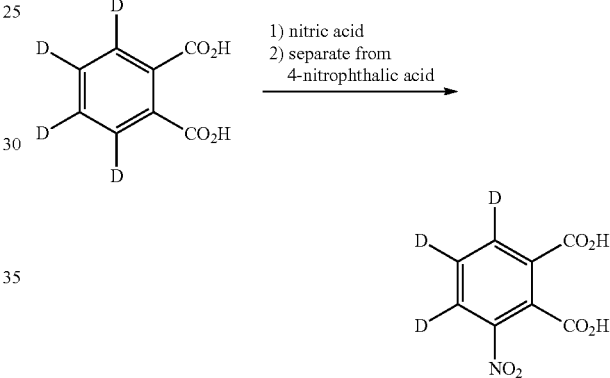

N15-A1

3-[$^{15}$N]nitrophthalic acid (N15-A1) is synthesized based on the procedures described in above for deuterated 3-nitrophthalic acid using phathlic acid and commercial available [$^{15}$N]nitric acid.

5.3.3 Deuterated A2

Deuterated 3-nitrophthalic acid, 10% Pd/C and ethanol is charged to a Parr hydrogenator under nitrogen atmosphere. Hydrogen is charged to the reaction vessel for up to 55 psi. The mixture is shaken for about 13 hours, while maintaining hydrogen pressure between 50 and 55 psi. Hydrogen is released and the mixture is purged with nitrogen 3 times. The suspension is filtered through a celite bed and rinsed with methanol. The filtrate is concentrated in vacuo. The resulting solid is reslurried in ether and isolated by vacuum filtration.

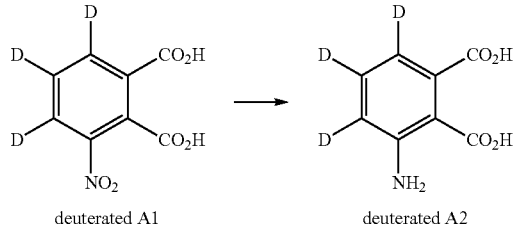 [SMILES: [2H]c1c([2H])c(C(=O)O)c(C(=O)O)c([N+](=O)[O-])c1[2H] ; [2H]c1c([2H])c(N)c(C(=O)O)c(C(=O)O)c1[2H]]

deuterated A1 → deuterated A2

In the alternative, A1 is subjected to conditions suitable for aromatic deuteration and reduction of the nitro group, which are known in the art. For example, A1 is treated with $D_2O$ over 5% Pt/C under hydrogen gas to provide deuterated A2.

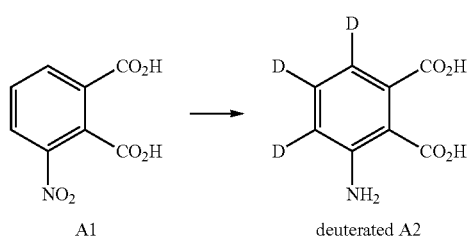

A1 → deuterated A2

5.3.4 N15-A2

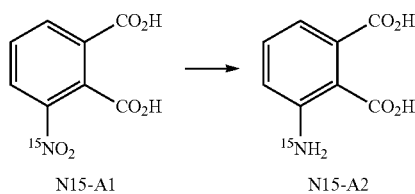

N15-A1 → N15-A2

3-[$^{15}$N]Aminophthalic acid (N15-A2) is synthesized based on the procedures described in Deuterated A2 using N15-A1.

5.3.5 Deuterated A3

Deuterated A2 and deuterated acetic anhydride, which is commercially available, is heated to reflux for about 3 hours and is cooled to ambient temperature and further to 0-5° C. for about another 1 hour. A crystalline solid is collected by vacuum filtration and is washed with ether. The solid product is dried in vacuo at ambient temperature to obtain deuterated A3.

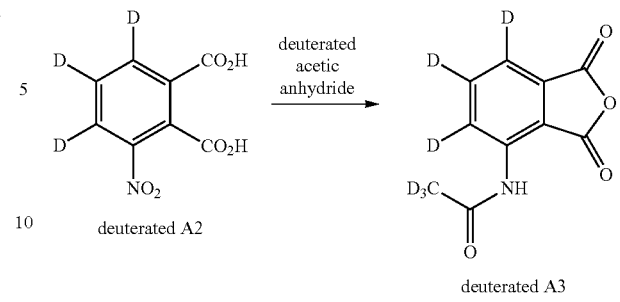

deuterated A2 → deuterated A3

5.3.6 N15-A3

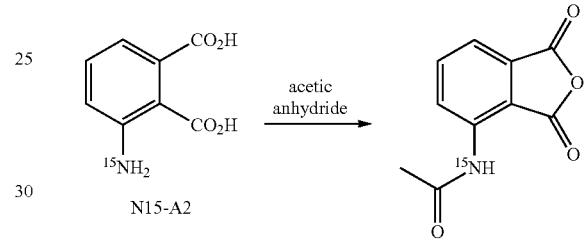

N15-A2 → N15-A3

N-(1,3-dioxo-1,3-dihydroisobenzofuran-4-yl)-[$^{15}$N]-acetamide (N15-A3) is synthesized based on the procedures described in Deuterated A3 using N15-A2 and acetic anhydride.

5.3.7 CD3-A3

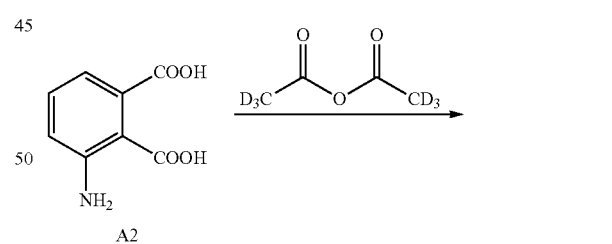

A2 → CD3-A3

N-(1,3-dioxo-1,3-dihydroisobenzofuran-4-yl)-[$^2H_3$]-acetamide (CD3-A3) is synthesized based on the procedures described in Deuterated A3 using A2 and [²H₃]acetic anhydride. Deuterated acetyl chloride may also be used.

5.3.8 Deuterated A4

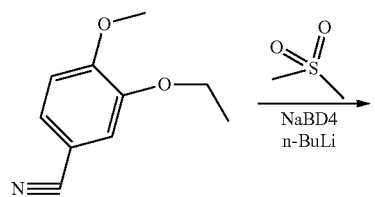

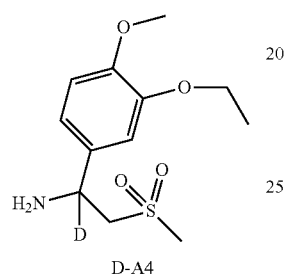

D-A4

1-(3-Ethoxy-4-methoxyphenyl)-2-(methylsulfonyl)-[1-²H]ethanamine (D-A4) is synthesized based upon the procedures described, for example, in Example 5.2 of U.S. Patent Publication No. US2010/0168475, using 3-ethoxy-4-methoxybenzonitrile, dimethylsulfone, n-BuLi and NaBD4. The product is further purified by column chromatography or crystallization.

5.3.9 3-Ethoxy-4-methoxybenzo[¹⁵N]nitrile

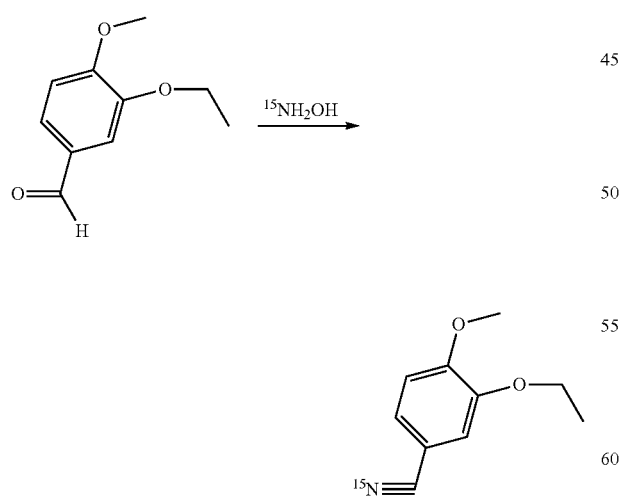

3-Ethoxy-4-methoxybenzo[¹⁵N]nitrile is synthesized based upon the procedures described, for example, in Example 5.1 of U.S. Patent Publication No. US2010/0168475 using 3-ethoxy-4-methoxybenzaldehyde and hydroxyl[¹⁵N]amine HCl. The product is further purified by column chromatography or crystallization.

5.3.10 N15-A4

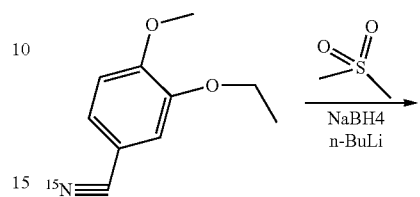

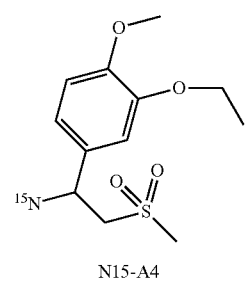

N15-A4

1-(3-Ethoxy-4-methoxyphenyl)-2-(methylsulfonyl)-ethan[¹⁵N]amine (N15-A4) is synthesized based upon the procedures described, for example, in Example 5.2 of U.S. Patent Publication No. US2010/0168475, using dimethylsulfone, n-BuLi, 3-ethoxy-4-methoxybenzo[¹⁵N]nitrile, and NaBH4. The product is further purified by column chromatography or crystallization.

5.3.11 C13-A4

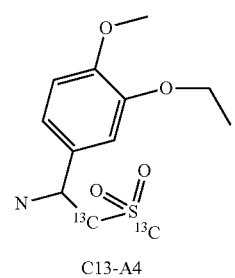

C13-A4

1-(3-Ethoxy-4-methoxyphenyl)-2-([¹³C]methylsulfonyl)[2-¹³C]ethanamine (C13-A4) is synthesized based upon the procedures described, for example, in Example 5.2 of U.S. Patent Publication No. US2010/0168475, using 3-ethoxy-4- methoxybenzonitrile, di[$^{13}$C]methylsulfone, n-BuLi and NaBH4. The product is further purified by column chromatography or crystallization.

5.3.12 Deuterated A5

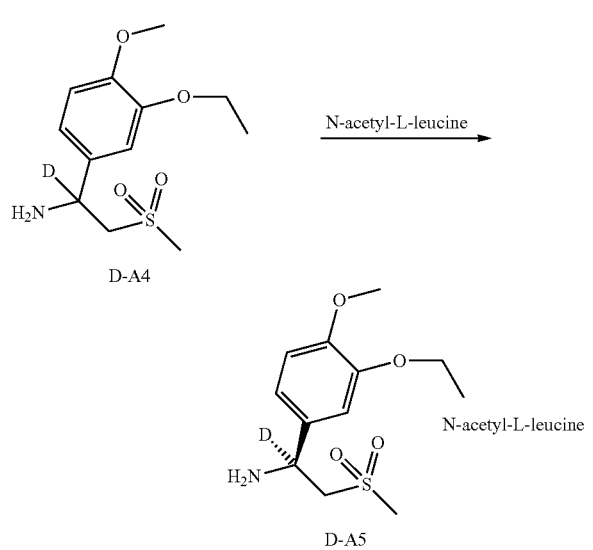

(S)-1-(3-Ethoxy-4-methoxyphenyl)-2-(methylsulfonyl)-[1-$^2$H]ethanamine N-acetyl-L-leucine (D-A5) is synthesized based upon the resolution procedures described, for example, in Example 5.2 of U.S. Pat. No. 6,962,940, using S-(3-ethoxy-4-methoxyphenyl)-2-(methylsulfonyl)-[1-$^2$H]ethanamine and N-acetyl-L-leucine.

5.3.13 N15-A5

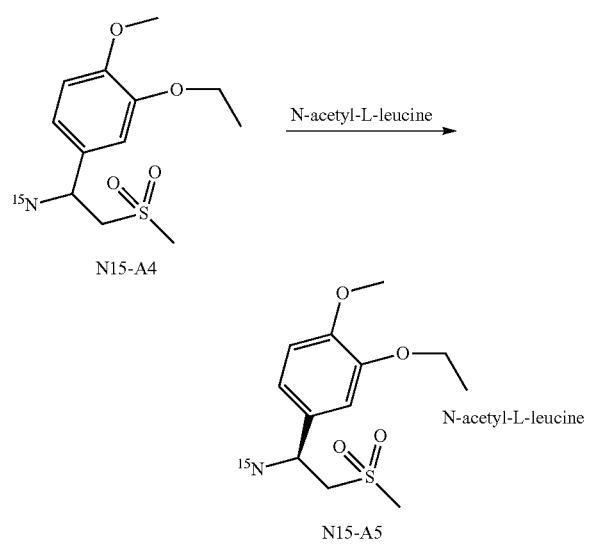

(S)-1-(3-Ethoxy-4-methoxyphenyl)-2-(methylsulfonyl) ethan[$^{15}$N]amine N-acetyl-L-leucine (N15-A5) is synthesized based upon the resolution procedures described, for example, in Example 5.2 of U.S. Pat. No. 6,962,940, using 1-(3-Ethoxy-4-methoxyphenyl)-2-(methylsulfonyl)ethan[$^{15}$N]amine and N-acetyl-L-leucine.

5.3.14 C13-A5

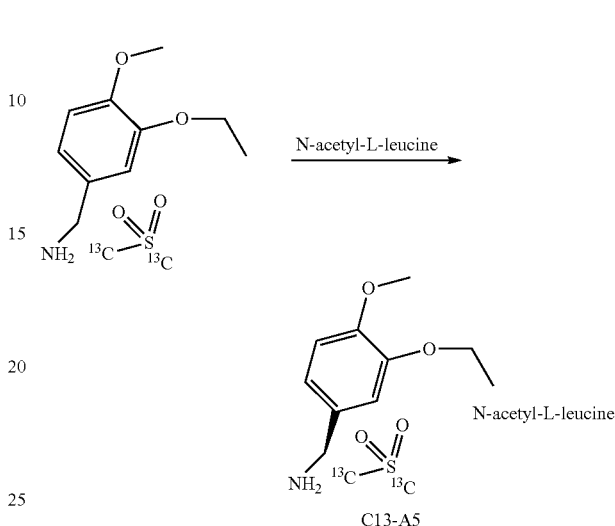

(S)-1-(3-Ethoxy-4-methoxyphenyl)-2-([$^{13}$C]methylsulfonyl)[2-$^{13}$C]ethanamine N-acetyl-L-leucine (C13-A5) is synthesized based upon the resolution procedures described, for example, in Example 5.2 of U.S. Pat. No. 6,962,940, using 1-(3-Ethoxy-4-methoxyphenyl)-2-([$^{13}$C]methylsulfonyl)-2-[$^{13}$C]ethanamine and N-acetyl-L-leucine.

5.4 Deuterated Compound V

Deuterated compound A5, which may be obtained via aromatic deuteration techniques known in the art, deuterated compound A3, and glacial acetic acid is refluxed overnight and then cooled to <50° C. The solvent is then removed in vacuo, and the residue is dissolved in ethyl acetate. The resulting solution is washed with water, saturated aqueous NaHCO$_3$, brine, and dried over sodium sulphate. The solvent is evaporated in vacuo, and the residue is recrystallized from a binary solvent containing ethanol and acetone. The solid is isolated by vacuum filtration and washed with ethanol. The product is then dried to afford deuterated compound V.

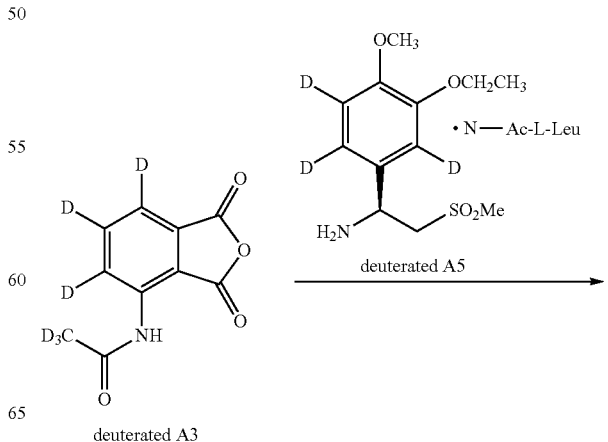

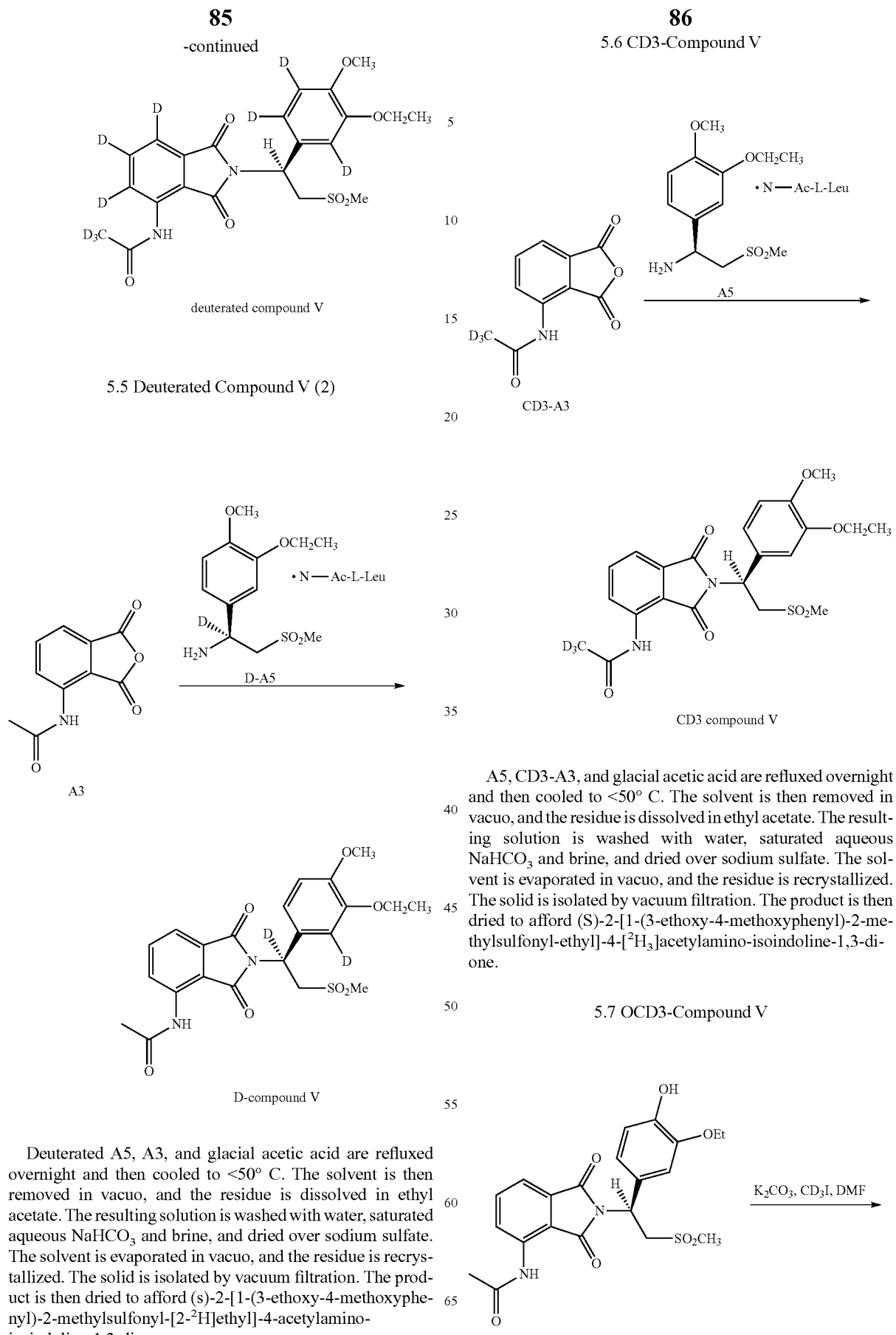

5.5 Deuterated Compound V (2)

Deuterated A5, A3, and glacial acetic acid are refluxed overnight and then cooled to <50° C. The solvent is then removed in vacuo, and the residue is dissolved in ethyl acetate. The resulting solution is washed with water, saturated aqueous NaHCO$_3$ and brine, and dried over sodium sulfate. The solvent is evaporated in vacuo, and the residue is recrystallized. The solid is isolated by vacuum filtration. The product is then dried to afford (s)-2-[1-(3-ethoxy-4-methoxyphenyl)-2-methylsulfonyl-[2-$^2$H]ethyl]-4-acetylamino-isoindoline-1,3-dione.

5.6 CD3-Compound V

A5, CD3-A3, and glacial acetic acid are refluxed overnight and then cooled to <50° C. The solvent is then removed in vacuo, and the residue is dissolved in ethyl acetate. The resulting solution is washed with water, saturated aqueous NaHCO$_3$ and brine, and dried over sodium sulfate. The solvent is evaporated in vacuo, and the residue is recrystallized. The solid is isolated by vacuum filtration. The product is then dried to afford (S)-2-[1-(3-ethoxy-4-methoxyphenyl)-2-methylsulfonyl-ethyl]-4-[$^2$H$_3$]acetylamino-isoindoline-1,3-dione.

5.7 OCD3-Compound V

-continued

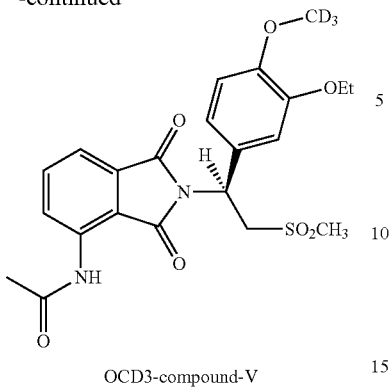

OCD3-compound-V (S)-N-(2-(1-(3-ethoxy-4-([²H₃]methoxy)-phenyl)-2-(methylsulfonyl)ethyl)-1,3-dioxoisoindolin-4-yl)acetamide (OCD3-compound V) is synthesized based on the procedures described in Example 5.2 above, using (S)-N-(2-(1-(3-ethoxy-4-hydroxyphenyl)-2-(methylsulfonyl)ethyl)-1,3-dioxoisoindolin-4-yl)acetamide, K₂CO₃ and [²H₃]methyl iodide in DMF. The product is purified by column chromatography or recrystallization.

5.8 N15-Compound V

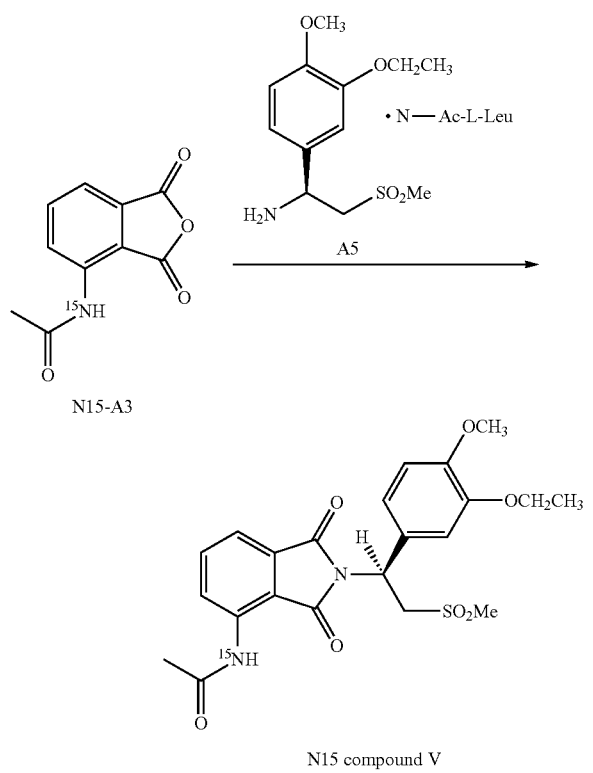

N15 compound V

Compound A5, N15-A3, and glacial acetic acid are refluxed overnight and then cooled to <50° C. The solvent is then removed in vacuo, and the residue is dissolved in ethyl acetate. The resulting solution is washed with water, saturated aqueous NaHCO₃ and brine, and dried over sodium sulfate. The solvent is evaporated in vacuo, and the residue is recrystallized. The solid is isolated by vacuum filtration. The product is then dried to afford (S)-2-[1-(3-Ethoxy-4-methoxyphenyl)-2-methylsulfonylethyl]-4-acetyl-[¹⁵N]aminoisoindoline-1,3-dione.

5.9 N15, N15-Compound V

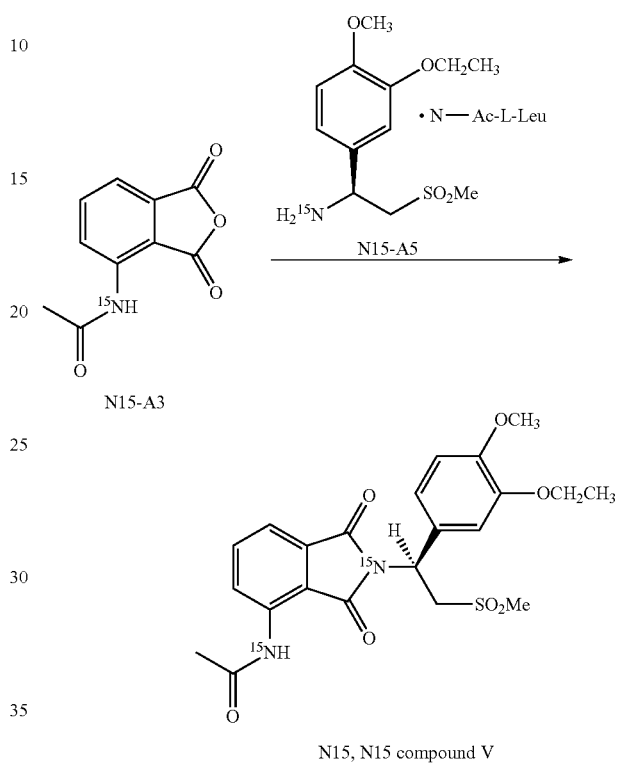

N15, N15 compound V

N15-A5, N15-A3, and glacial acetic acid are refluxed overnight and then cooled to <50° C. The solvent is then removed in vacuo, and the residue is dissolved in ethyl acetate. The resulting solution is washed with water, saturated aqueous NaHCO₃ and brine, and dried over sodium sulfate. The solvent is evaporated in vacuo, and the residue is recrystallized. The solid is isolated by vacuum filtration. The product is then dried to afford (S)-2-[1-(3-ethoxy-4-methoxyphenyl)-2-methylsulfonylethyl]-4-acetyl-([¹⁵N]amino)-isoindoline-[2-¹⁵N]-1,3-dione.

5.10 Deuterated Compound IX

Compound IX is synthesized following the methods disclosed in U.S. Pat. No. 6,667,316. Compound IX is subsequently subjected to aromatic deuteration conditions to afford deuterated compound IX.

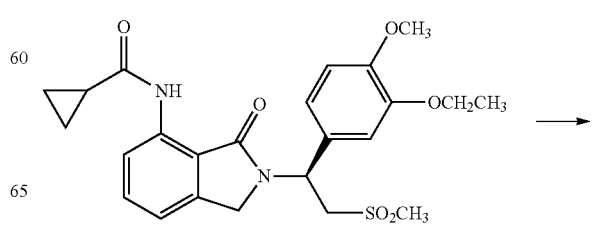

-continued

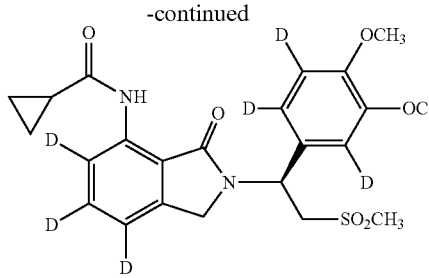

5.11 7-Deuterated Compound IX

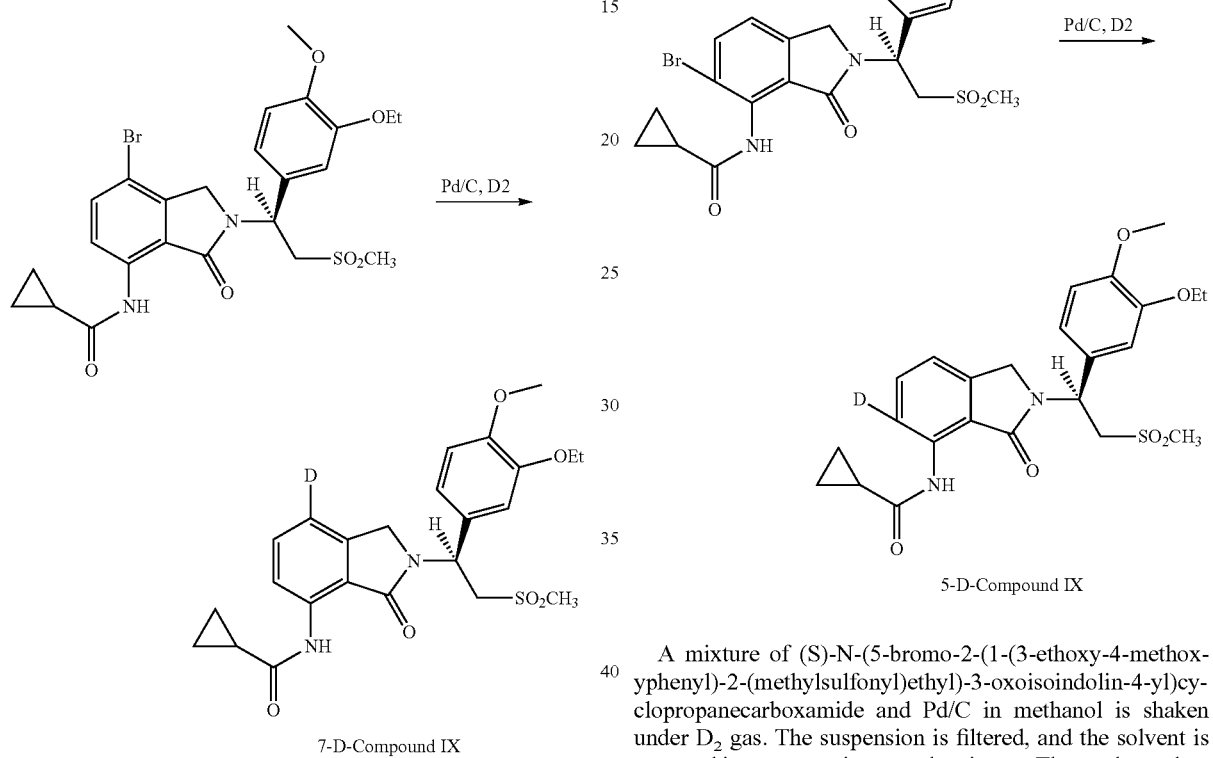

7-D-Compound IX

A mixture of (S)-N-(7-bromo-2-(1-(3-ethoxy-4-methoxyphenyl)-2-(methylsulfonyl)ethyl)-3-oxoisoindolin-4-yl)cyclopropanecarboxamide and Pd/C in methanol is shaken under $D_2$ gas. The suspension is filtered, and the solvent is removed in vacuo to give a crude mixture. The crude product is purified by column chromatography or recrystallization to give (S)-N-(2-(1-(3-ethoxy-4-methoxyphenyl)-2-(methylsulfonyl)ethyl)-3-oxo-[7-$^2$H]-isoindolin-4-yl)cyclopropanecarboxamide.

5.12 5-Deuterated Compound IX

5-D-Compound IX

A mixture of (S)-N-(5-bromo-2-(1-(3-ethoxy-4-methoxyphenyl)-2-(methylsulfonyl)ethyl)-3-oxoisoindolin-4-yl)cyclopropanecarboxamide and Pd/C in methanol is shaken under $D_2$ gas. The suspension is filtered, and the solvent is removed in vacuo to give a crude mixture. The crude product is purified by column chromatography or recrystallization to give (S)-N-(2-(1-(3-ethoxy-4-methoxyphenyl)-2-(methylsulfonyl)ethyl)-3-oxo-[5-$^2$H]isoindolin-4-yl)cyclopropanecarboxamide.

5.13 Deuterated Compound IX (2)

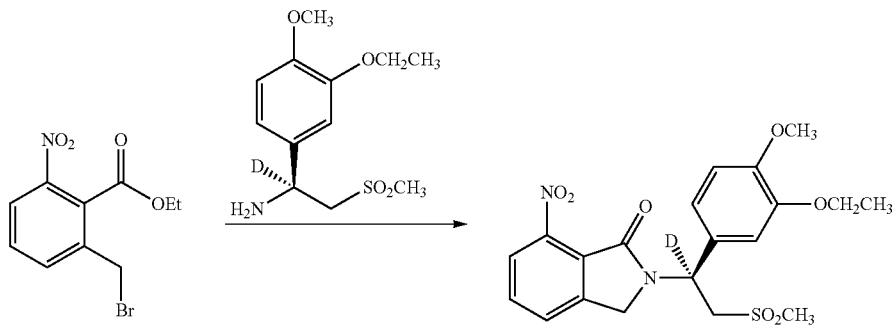

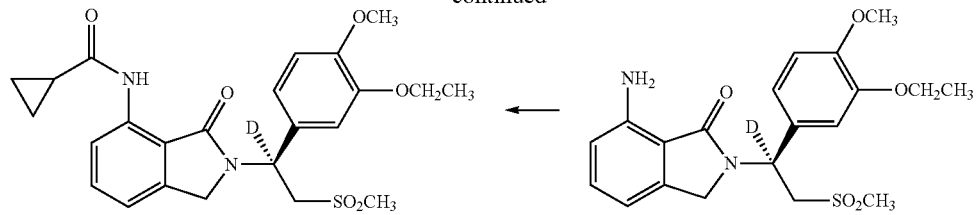

-continued

A mixture of ethyl 2-(bromomethyl)-6-nitrobenzoate and (S)-1-(3-ethoxy-4-methoxyphenyl)-2-(methylsulfonyl)[1-$^2$H]ethanamine, triethyl amine in DMF is heated to refluxed. The solvent is removed in vacuo. The crude mixture is purified by column chromatography to give (S)-2-(1-(3-ethoxy-4-methoxyphenyl)-2-(methylsulfonyl)[1-$^2$H]ethyl)-7-nitroisoindolin-1-one. A mixture of (S)-2-(1-(3-ethoxy-4-methoxyphenyl)-2-(methylsulfonyl)[1-$^2$H]ethyl)-7-nitroisoindolin-1-one and Pd/C in ethyl acetate is shaken under hydrogen. The suspension is filtered thru a pad of Celite. The solvent is removed in vacuo. The crude mixture is purified by column chromatography to give (S)-7-amino-2-(1-(3-ethoxy-4-methoxyphenyl)-2-(methylsulfonyl)-[1-$^2$H]ethyl)isoindolin-1-one.

(S)-N-(2-(1-(3-ethoxy-4-methoxyphenyl)-2-(methylsulfonyl)-[1-$^2$H]ethyl)-3-oxoisoindolin-4-yl)cyclopropanecarboxamide is synthesized based upon the procedures described, for example, in Example 7 of U.S. Pat. No. 6,667,316, starting from (S)-7-amino-2-(1-(3-ethoxy-4-methoxyphenyl)-2-(methylsulfonyl)-[1-$^2$H]ethyl)isoindolin-1-one. The product is further purified by column chromatography or crystallization.

5.14 OCD3-Compound IX

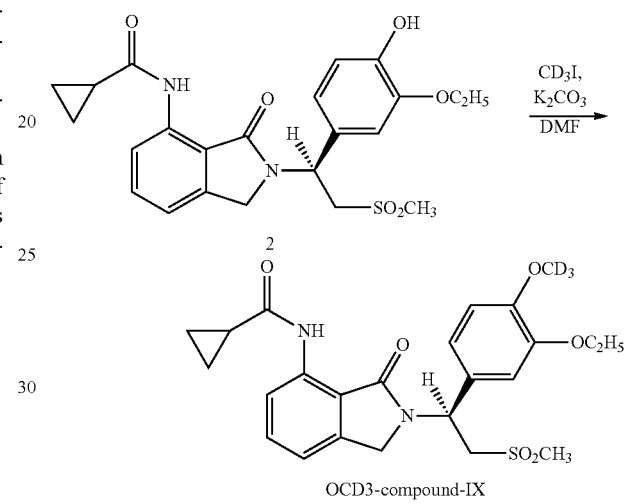

OCD3-compound-IX (S)-N-(2-(1-(3-ethoxy-4-([$^2$H$_3$]methoxy)-phenyl)-2-(methylsulfonyl)ethyl)-3-oxoisoindolin-4-yl)cyclopropanecarboxamide (OCD3-compound IX) is synthesized based on the procedures described in Example 5.1 above, using (S)-N-(2-(1-(3-ethoxy-4-hydroxyphenyl)-2-(methylsulfonyl)ethyl)-3-oxoisoindolin-4-yl)cyclopropanecarboxamide, K$_2$CO$_3$ and [$^2$H$_3$]methyl iodide in DMF. The product is purified by column chromatography or recrystallization.

5.15 N15-Compound IX

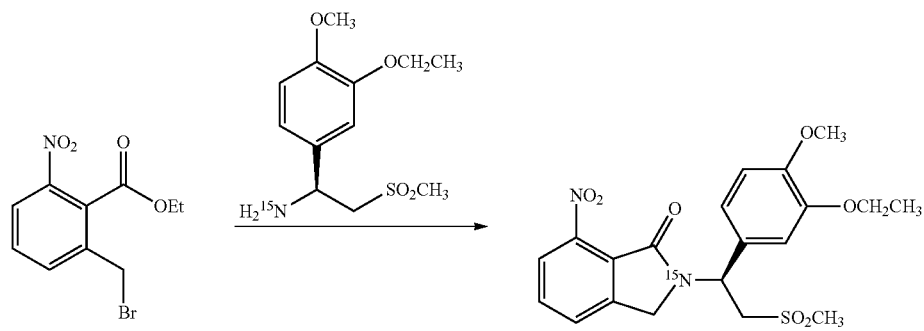

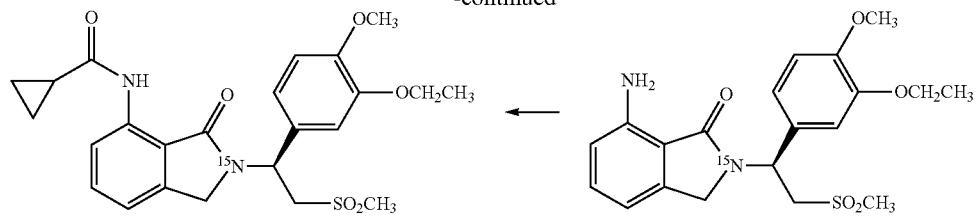

A mixture of ethyl 2-(bromomethyl)-6-nitrobenzoate and (S)-1-(3-ethoxy-4-methoxyphenyl)-2-(methylsulfonyl)ethan[15N]amine, triethyl amine in DMF is heated to reflux. The solvent is removed in vacuo. The crude mixture is purified by column chromatography to give (S)-2-(1-(3-ethoxy-4-methoxyphenyl)-2-(methylsulfonyl)ethyl)-7-nitro[15N]isoindolin-1-one. A mixture of (S)-2-(1-(3-ethoxy-4-methoxyphenyl)-2-(methylsulfonyl)ethyl)-7-nitro[15N]isoindolin-1-one and Pd/C in ethyl acetate is shaken under hydrogen. The suspension is filtered thru a pad of Celite. The solvent is removed in vacuo. The crude mixture is purified by column chromatography to give (S)-7-amino-2-(1-(3-ethoxy-4-methoxyphenyl)-2-(methylsulfonyl)ethyl)[15N]isoindolin-1-one.

(S)-N-(2-(1-(3-ethoxy-4-methoxyphenyl)-2-(methylsulfonyl)ethyl)-3-oxo[15N]isoindolin-4-yl)cyclopropanecarboxamide is synthesized based upon the procedures described, for example, in Example 7 of U.S. Pat. No. 6,667,316, starting from (S)-7-amino-2-(1-(3-ethoxy-4-methoxyphenyl)-2-(methylsulfonyl)ethyl)[15N]isoindolin-1-one. The product is further purified by column chromatography or crystallization.

5.16 C13-Compound IX

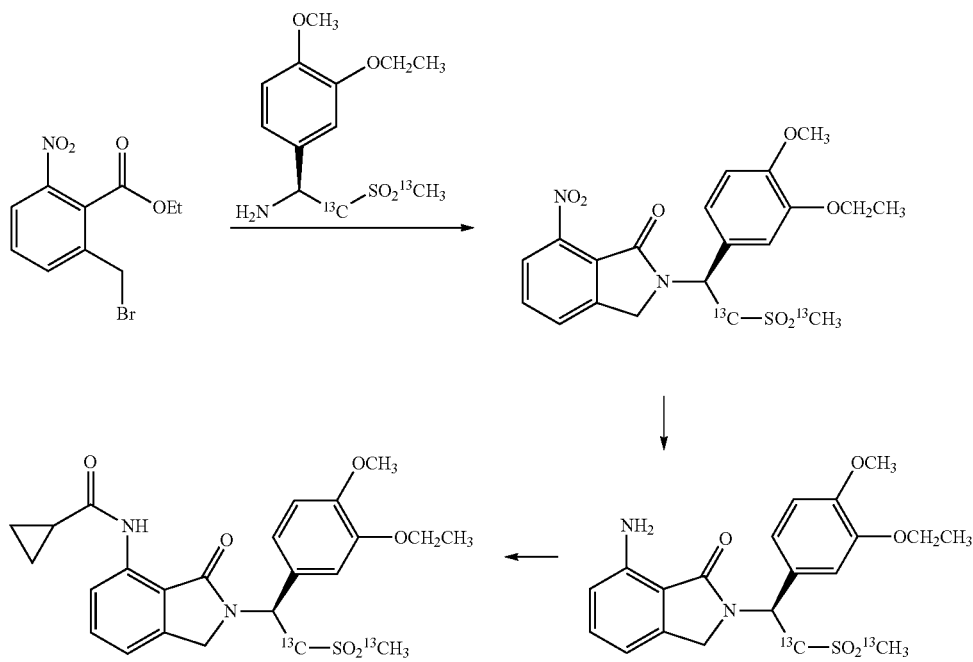

A mixture of ethyl 2-(bromomethyl)-6-nitrobenzoate and (S)-1-(3-ethoxy-4-methoxyphenyl)-2-([13C]methylsulfonyl)[2-13C]ethanamine, triethyl amine in DMF is heated to reflux. The solvent is removed in vacuo. The crude mixture is purified by column chromatography to give (S)-2-(1-(3-ethoxy-4-methoxyphenyl)-2-([13C]methylsulfonyl)[2-13C]ethyl)-7-nitroisoindolin-1-one. A mixture of (S)-2-(1-(3-ethoxy-4-methoxyphenyl)-2-([13C]methylsulfonyl) [2-13C]ethyl)-7-nitroisoindolin-1-one and Pd/C in ethyl acetate is shaken under hydrogen. The suspension is filtered thru a pad of Celite. The solvent is removed in vacuo. The crude mixture is purified by column chromatography to give (S)-7-amino-2-(1-(3-ethoxy-4-methoxyphenyl)-2-([13C]methylsulfonyl)[2-13C]ethyl)isoindolin-1-one.

(S)-N-(2-(1-(3-ethoxy-4-methoxyphenyl)-2-[13C]methylsulfonyl)[2-13C]ethyl)-3-oxoisoindolin-4-yl)cyclopropanecarboxamide is synthesized based upon the procedures described, for example, in Example 7 of U.S. Pat. No. 6,667,316, starting from (S)-7-amino-2-(1-(3-ethoxy-4-methoxyphenyl)-2-([13C]methylsulfonyl)[2-13C]ethyl)isoindolin-1-one. The product is further purified by column chromatography or crystallization.

5.17 Determination of Isotopic Enrichment

Isotopic enrichment may be confirmed and quantified by mass spectrometry and/or NMR, including, for example, proton-NMR; carbon-13 NMR; or nitrogen-15 NMR.

Isotopic enrichment may also be confirmed by single-crystal neutron diffraction. For example, the isotopic ratio at a particular hydrogen/deuterium position in a deuterated compound can be determined using single-crystal neutron diffraction. Neutron diffraction is advantageous because neutrons are scattered by the nucleus of an atom, therefore allowing for discrimination between isotopes, such as hydrogen and deuterium, that differ in the number of neutrons in the nucleus.

A single crystal of suitable size and quality comprising the deuterated compound is grown using standard methods of crystal growth. For single-crystal neutron diffraction experiments, crystals of several cubic millimeters are generally required for suitable data collection. A minimum size for a single crystal is typically about 1 cubic millimeter. Suitable single crystals are obtained by dissolving the deuterated compound in a solvent with appreciable solubility, then slowly evaporating or cooling the solution to yield crystals of suitable size and quality. Alternatively, suitable single crystals are obtained by dissolving the deuterated compound in a solvent with appreciable solubility, then slowly diffusing into the solution of antisolvent (i.e., a solvent in which the deuterated compound is not appreciably soluble) to yield crystals of suitable size and quality. These and other suitable methods of crystal growth are known in the art and are described, e.g., in George H. Stout & Lyle H. Jensen. X-Ray Structure Determination: A Practical Guide 74-92 (John Wiley & Sons, Inc. 2nd ed. 1989) (the entirety of which is incorporated herein).

After isolating a suitable single crystal comprising the deuterated compound, the crystal is mounted in a neutron beam, neutron diffraction data is collected, and the crystal structure is solved and refined. Different neutron sources can be used, including steady-state sources and pulsed spallation sources. Examples of steady-state sources include the Grenoble ILL High Flux Reactor (Grenoble, France) and the Oak Ridge High Flux Isotope Reactor (Oak Ridge, Tenn.). Examples of pulsed spallation sources include ISIS, the spallation neutron source at Rutherford Appleton Laboratory (Oxfordshire, UK); the Intense Pulsed Neutron Source (IPNS) at Argonne National Laboratory (Argonne, Ill.), the Los Alamos Neutron Science Center (LANSCE) at Los Alamos National Laboratory (Los Alamos, N. Mex.), and the Neutron Science Laboratory (KENS) at KEK (Tsukuba, Ibaraki, Japan).

For a steady-state neutron source, four-circle diffractometer techniques are used with a monochromatic beam and a single detector, rotating the crystal and detector to measure each reflection sequentially. Diffractometer control software and step-scanning methods for intensity extraction can be adopted from routine four-circle X-ray diffractometry methods. One or more area detectors, including area detector arrays, may alternatively be used to increase the region of reciprocal space accessed in a single measurement. A broad band (white) beam used with an area detector allows for Laue or quasi-Laue diffraction with a stationary crystal and detector.

For a pulse source with a white neutron beam, time-of-flight Laue diffraction techniques are used, which allow for the determination of the velocity, energy, and wavelength of each neutron detected. This approach combines wavelength sorting with large area position-sensitive detectors, and allows for fixed scattering geometries (i.e. a stationary crystal and detector). Pulse source data collected in this fashion allows for rapid collection of data sets and good accuracy and precision in standard structural refinements. Additional details regarding steady-state and pulse source neutron diffraction experiments are well known in the art. See, e.g., Chick C. Wilson, *Neutron Single Crystal Diffraction*, 220 Z. Kristallogr, 385-98 (2005) (incorporated by reference herein in its entirety).

Crystal structure data, including particular isotopic ratios, are obtained from neutron diffraction data following routine structure solution and refinement processes. Structure solution is carried out using one of several methods, including direct methods and Patterson methods. For convenience, atomic coordinates from prior single crystal X-ray diffraction experiments may be used as a starting point for structure refinement using neutron diffraction data; this approach permits additional refinement of atomic positions, including hydrogen and deuterium positions. Refinement is conducted using full-matrix least-squares methods to achieve optimal agreement between the observed diffraction intensities and those calculated from the structural model. Ideally, full anisotropic refinement is carried out on all atoms, including the H/D atomic positions of interest. Data collection, structure solution and structure refinement methods, both for X-ray and neutron diffraction data, are well known in the art. See, e.g., Chick C. Wilson. Single Crystal Neutron Diffraction from Molecular Materials (World Scientific Publishing Co. 2000); George H. Stout & Lyle H. Jensen, X-Ray Structure Determination: A Practical Guide (John Wiley & Sons. Inc. 2nd ed. 1989) (both of which are incorporated herein in their entireties).

The isotopic ratio for a particular position on a deuterated compound is calculated by examining the neutron scattering cross sections for the H/D atomic position of interest. The scattering cross section is obtained as part of the refinement process discussed above. An example of determining the isotopic ratio for a partially deuterated compound is provided by G. A. Jeffrey et al., *Neutron Diffraction Refinement of Partially Deuterated β-D-Arabinopyranose and α-L-Xylopyranose at 123 K*, B36 Acta Crystallographica 373-77 (1980) (incorporated by reference herein in its entirety). Jeffrey et al., used single-crystal neutron diffraction to determine the percentage deuterium substitution for hydroxyl groups on two sugar compounds of interest. Employing the methods discussed by Jeffrey et al., one may similarly ascertain the isotopic ratio for a particular H/D position on a deuterated compound.

All of the cited references are incorporated herein by reference in their entirety.

What is claimed is:
1. A compound of formula:

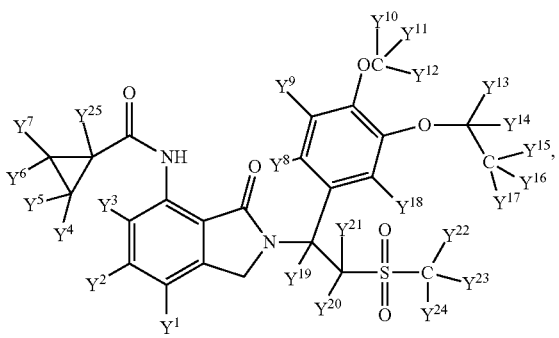

or a pharmaceutically acceptable salt thereof, wherein:
at least one of $Y^1$-$Y^{25}$ is a hydrogen that is isotopically enriched with deuterium, and the others of $Y^1$-$Y^{25}$ are non-enriched hydrogen atoms.

2. The compound of claim 1, wherein the compound is an (S)-isomer having a structure:

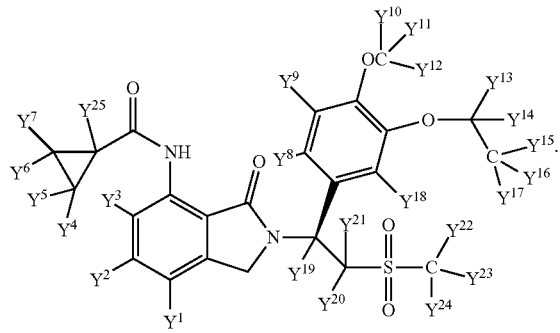

3. The compound of claim 1, wherein one to five of $Y^1$-$Y^{25}$ is isotopically enriched with deuterium, and the others are non-enriched hydrogens.

4. The compound of claim 1, wherein six to ten of $Y^1$-$Y^{25}$ are isotopically enriched with deuterium, and the others are non-enriched hydrogens.

5. The compound of claim 1, wherein eleven to fifteen of $Y^1$-$Y^{25}$ are isotopically enriched with deuterium, and the others are non-enriched hydrogens.

6. The compound of claim 1, wherein sixteen to twenty of $Y^1$-$Y^{25}$ are isotopically enriched with deuterium, and the others are non-enriched hydrogens.

7. The compound of claim 1, wherein twenty one to twenty five of $Y^1$-$Y^{25}$ are isotopically enriched with deuterium, and the others are non- enriched hydrogens.

8. A pharmaceutical composition comprising a compound of claim 1 or a pharmaceutically acceptable salt thereof.

9. A method of inhibiting TNFα or PDE4 levels in a patient comprising administering to a patient a compound of claim 1, or a pharmaceutically acceptable salt or thereof.

10. The method of claim 9, further comprising administering a second active agent selected from prednisone, salicylic acid acetate, clarithromycin, bortezomib, and dexamethasone.

* * * * *